(12) United States Patent
Ishihara et al.

(10) Patent No.: US 7,889,228 B2
(45) Date of Patent: Feb. 15, 2011

(54) SIGNAL PROCESSING DEVICE FOR ENDOSCOPE

(75) Inventors: Hideaki Ishihara, Hachioji (JP);
Takayuki Hanawa, Hachioji (JP);
Nobuyuki Doguchi, Hino (JP);
Fumiyuki Okawa, Hino (JP)

(73) Assignee: Olympus Corporation, Tokyo (JP)

( * ) Notice: Subject to any disclaimer, the term of this patent is extended or adjusted under 35 U.S.C. 154(b) by 1232 days.

(21) Appl. No.: 11/497,742

(22) Filed: Aug. 2, 2006

(65) Prior Publication Data

US 2007/0002134 A1 Jan. 4, 2007

Related U.S. Application Data

(63) Continuation of application No. PCT/JP2005/01520, filed on Feb. 2, 2005.

(30) Foreign Application Priority Data

Feb. 4, 2004 (JP) .............................. 2004-028426

(51) Int. Cl.
 *H04N 7/18* (2006.01)
 *A61B 1/04* (2006.01)
(52) U.S. Cl. ........................................ 348/65; 600/118
(58) Field of Classification Search .................... 348/65, 348/72; 600/104, 118, 134; *H04N 7/18; A61B 1/04*
See application file for complete search history.

(56) References Cited

U.S. PATENT DOCUMENTS

| 5,105,276 | A | 4/1992 | Schrock |
| 5,337,340 | A | 8/1994 | Hynecek |
| 2004/0143157 | A1 | 7/2004 | Doguchi et al. |

2005/0020879 A1* 1/2005 Suzuki ...................... 600/118

FOREIGN PATENT DOCUMENTS

| EP | 1 099 405 A1 | 5/2001 |
| EP | 1 143 706 A2 | 10/2001 |
| JP | 07-021753 | 1/1995 |
| JP | 08-009223 | 1/1996 |

(Continued)

OTHER PUBLICATIONS

Supplementary European Search Report dated May 26, 2010.

*Primary Examiner*—Gims S Philippe
(74) *Attorney, Agent, or Firm*—Scully, Scott, Murphy & Presser, P.C.

(57) ABSTRACT

An endoscope includes a solid image-pickup device having an image area and an optical black area for performing photoelectric conversion and including a function of varying an amplification ratio, and a first signal clamp circuit clamps the analog output signal that is outputted from the solid image-pickup device to adjust into an input range of the analog signal processing circuit with an analog reference signal which is unaffected by a defective pixel in the optical black area. The clamped signal is processed to extract signal components which are photoelectrically converted by the analog signal processing circuit by the image area. The output signal from the analog signal processing circuit clamps the signal in the optical black area by using output signals of at least the number of pixels larger than the number of pixels in a horizontal direction in the optical black area by the second signal clamp circuit.

20 Claims, 14 Drawing Sheets

FOREIGN PATENT DOCUMENTS

| | | |
|---|---|---|
| JP | 10-276976 | 10/1998 |
| JP | 2000-350194 | 12/2000 |
| JP | 2001-029313 | 2/2001 |
| JP | 3284673 | 3/2002 |
| JP | 2003-134400 | 5/2003 |
| WO | WO00/69324 | 11/2000 |

* cited by examiner

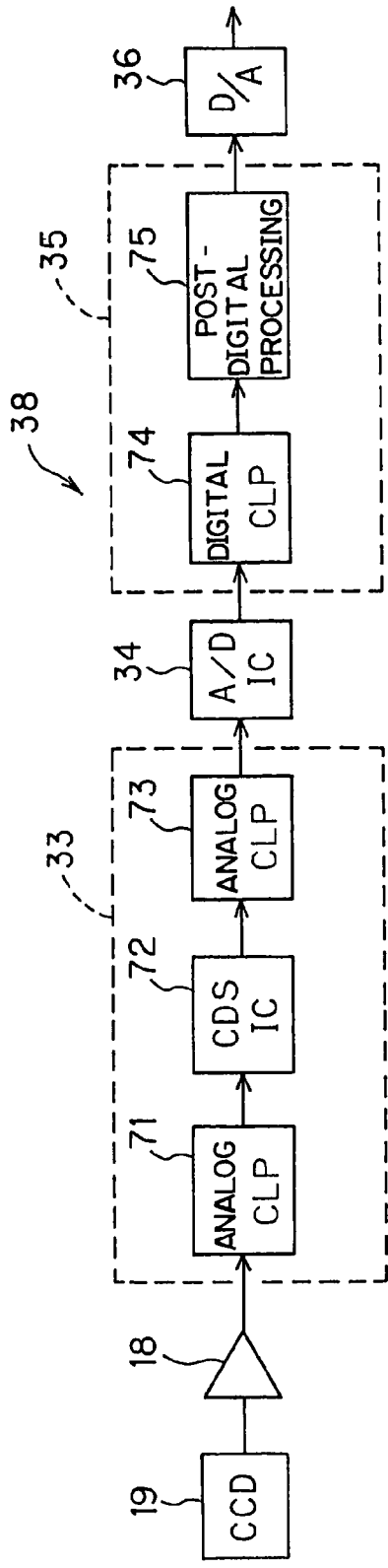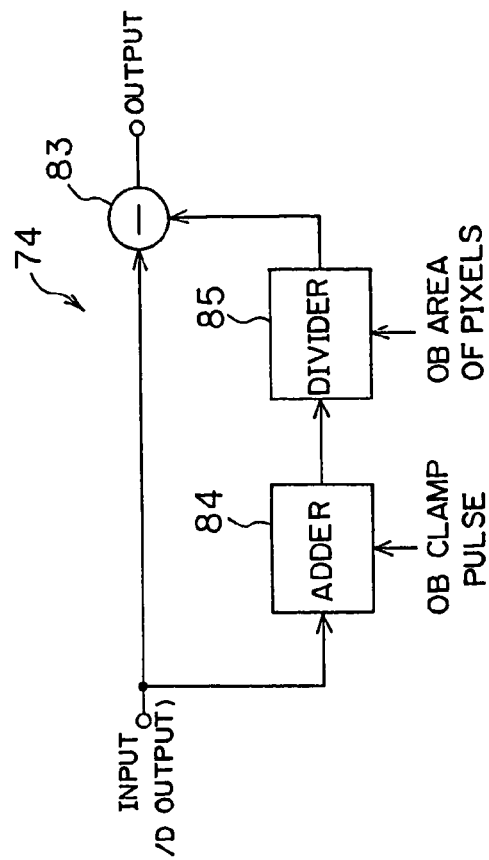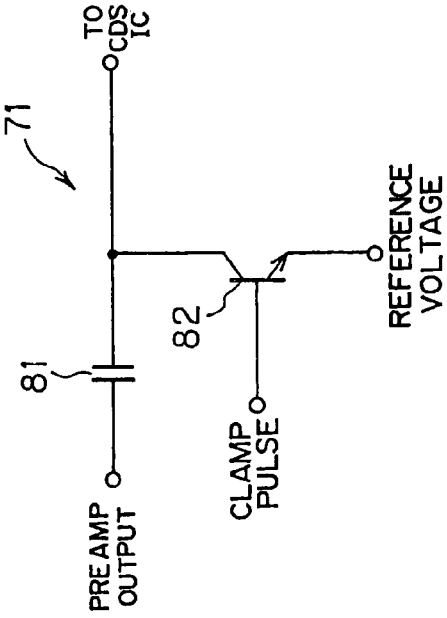

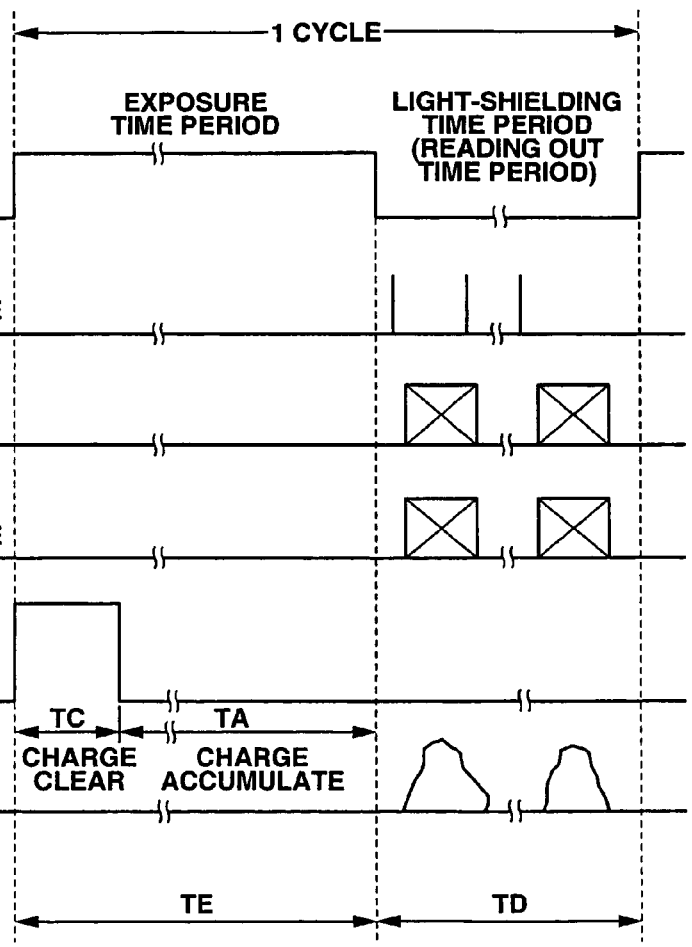

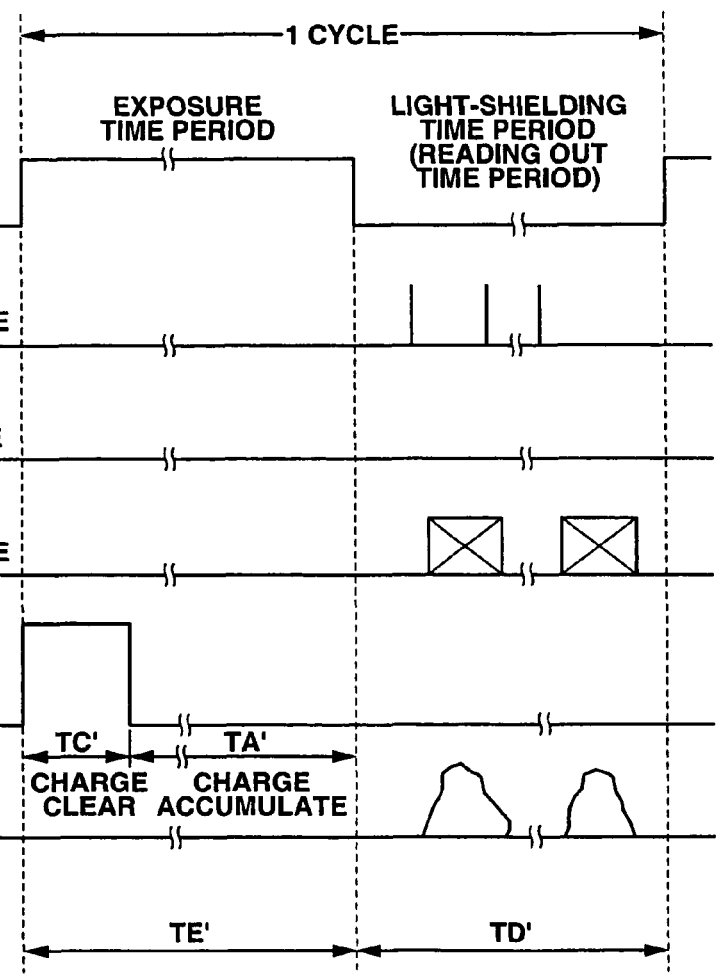

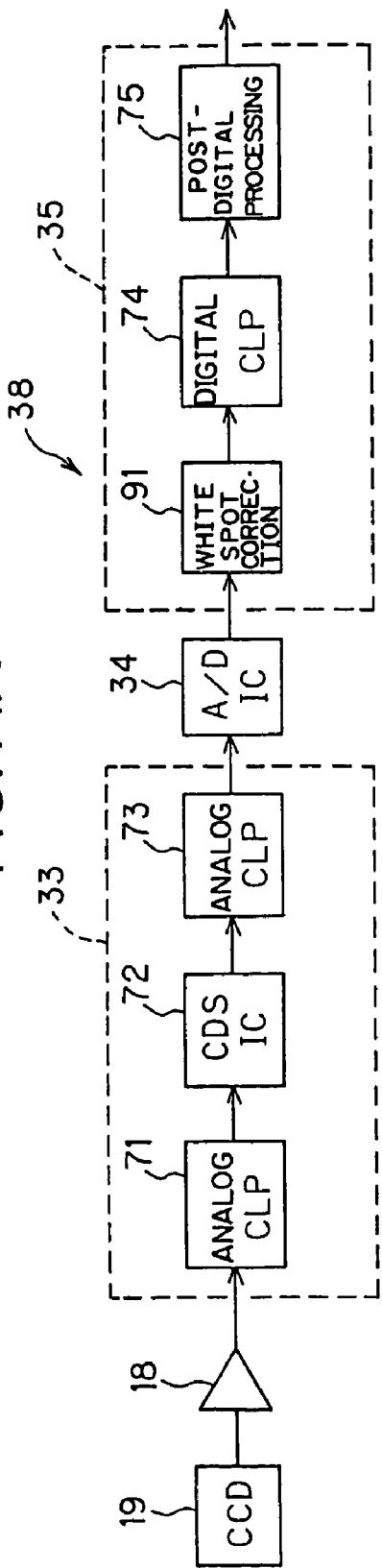
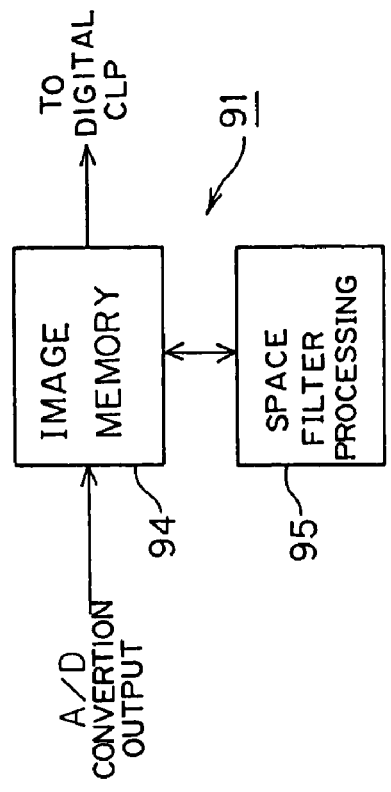
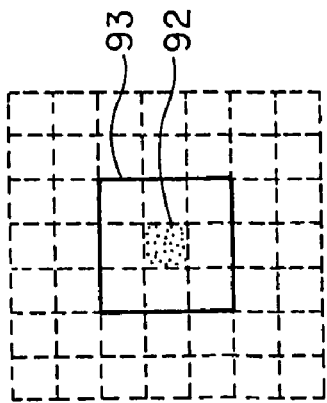

FIG.15A
PRIOR ART
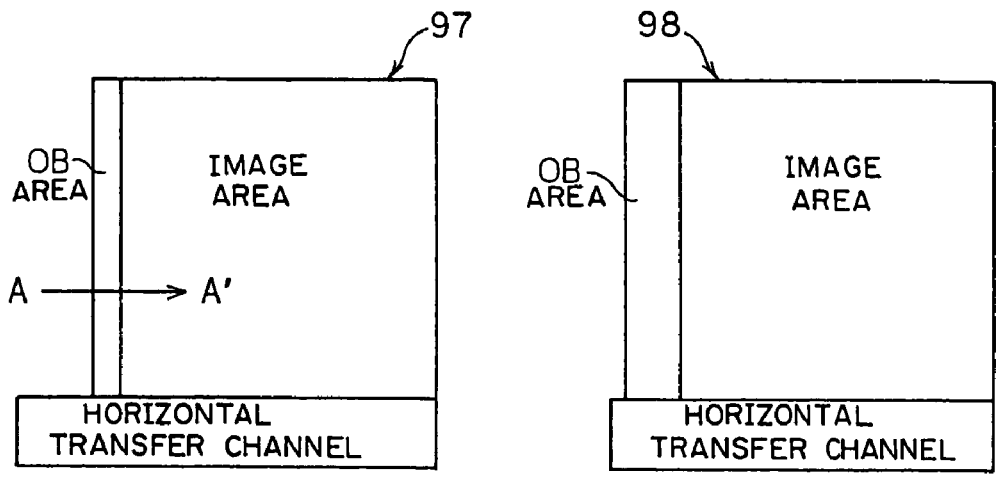
FIG.15B
PRIOR ART
FIG.15C
PRIOR ART
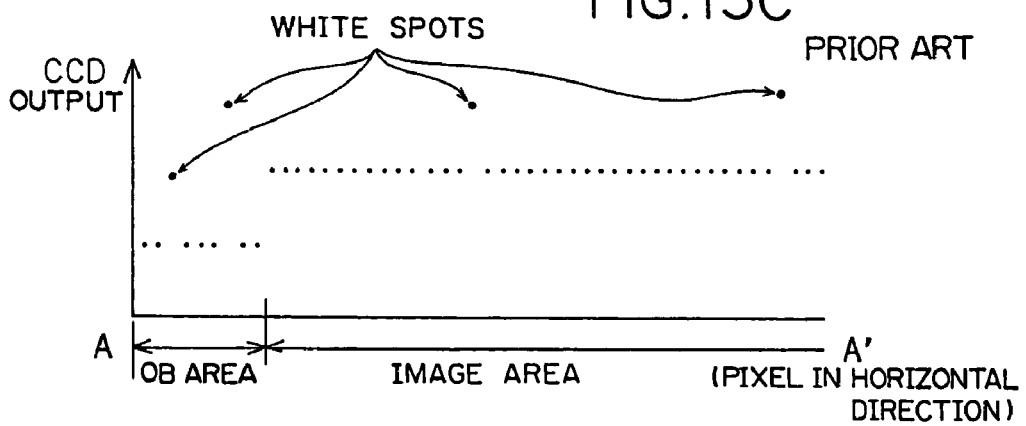
FIG.15D
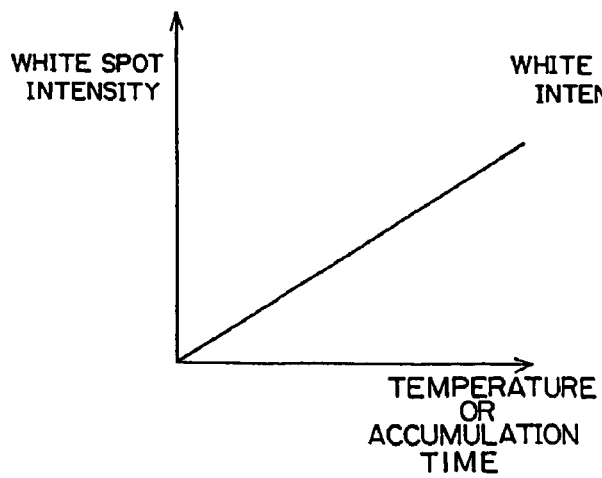
FIG.15E
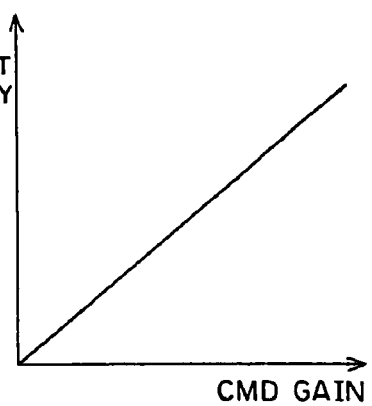

SIGNAL PROCESSING DEVICE FOR ENDOSCOPE

CROSS REFERENCE TO RELATED APPLICATION

This application is a continuation application of PCT/JP2005/001520 filed on Feb. 2, 2005 and claims benefit of Japanese Application No. 2004-028426 filed in Japan on Feb. 4, 2004, the entire contents of which are incorporated herein by this reference.

BACKGROUND OF THE INVENTION

1. Field of the Invention

The present invention relates to a signal processing device for an endoscope which performs signal processing on an image-pickup device included in the endoscope.

2. Description of the Related Art

Electronic endoscopes including a solid image-pickup device at the distal portion of the inserting section of the endoscope have been widespread. For example, as disclosed in Japanese Patent Laid-Open No. 2001-29313, there has been proposed an electronic endoscope including a solid image-pickup device with an amplifying function inside the solid image-pickup device. As in the precedent example, an electronic endoscope with an amplifying function inside a solid image-pickup device can perform variable control on a signal level of an output signal that is outputted from the solid image-pickup device by applying an amplification ratio control signal for performing variable control on an amplification ratio (or sensitivity) from a signal processing device side, and therefore it has an advantage of obtaining an image with a good S/N even in a gleam such as in a fluorescent observation.

When a solid image-pickup device which can vary an amplification ratio by applying such an amplification ratio control signal is housed at the tip of an electronic endoscope, it is desirable to house the device by reducing it in size as small as possible as in the case of a usual solid image-pickup device.

For that purpose, as a charge coupled device (abbreviated as CCD) 97 which is included in a conventional electronic endoscope and can vary an amplification ratio, as shown in FIG. 15A, one with a narrowed horizontal width (number of pixels) in an optical black area (abbreviated as OB area) compared to a CCD98 (see FIG. 15B) (which does not need to be reduced in size as compared with the case where it is included in an endoscope) is adopted.

When a signal charge accumulated in an image area by using the CCD97 is read out via a horizontal transfer channel, it results in as shown in FIG. 15C, for example. As it is shown in FIG. 15C, the read out output signal may include a pixel which greatly deviates to higher level from a normal photoelectric conversion level, i.e., a defective pixel.

Such a defective pixel is usually called a white spot. The white spot occurs due to impurities in a photo diode being formed. The white spot exhibits characteristics which depend on temperature. The higher the temperature, the greater the white spot's influence is. Specifically, as shown in FIG. 15D, the intensity of a white spot (output level) increases almost in proportion to temperature.

The intensity of a white spot increases as an amplification ratio or an accumulation time increases. More specifically, as shown in FIG. 15E, the intensity increases almost in proportion to an amplification ratio.

As it has characteristics like that, it is desirable to reduce an influence of a white spot in a medical electronic endoscope which is inserted in a human body for endoscope examination and used in a state at a temperature higher than a room temperature. Although it is also conceivable that it is cooled by a Peltier device, the Peltier device causes the tip of the inserting section of the electronic endoscope to be thicker.

If an endoscope image is obtained by signal processing using the CCD97, the CCD output signal is inputted to a CDS circuit which performs correlation double sampling (abbreviated as CDS). The CCD output signal needs to be subject to analog clamping at the previous stage so as to be adjusted to an input range of the CDS circuit.

In the precedent example, if it is inputted into an analog signal processing circuit such as a CDS circuit or the like, it was clamped in an optical black (abbreviated as OB) area of the CCD97. Therefore, if a white spot is present in the OB area, it is clamped at a potential level higher than the potential level which originally needs to be clamped. That relatively decreases an output level of an image area and degradation of an image quality such as appearance of black lines in an image occurs (explained again in FIG. 6B as described later).

SUMMARY OF THE INVENTION

The present invention is characterized by comprising:

an analog signal processing circuit that processes an analog output signal outputted from a solid image-pickup device, which has an image area and an optical black area performing photoelectric conversion, includes a function of varying an amplification ratio, and is mounted on an endoscope, to extract signal components photoelectrically converted by the image area;

a first signal clamp circuit for clamping an analog reference signal which is unaffected by a defective pixel in the optical black area so as to adjust into an input range of the analog signal processing circuit and inputting it to the analog signal processing circuit; and a second signal clamp circuit for, with respect to the output signal from the analog signal processing circuit, clamping the signal in the optical black area using output signals of at least the number of pixels larger than the number of pixels in a horizontal direction in the optical black area.

BRIEF DESCRIPTION OF THE DRAWINGS

FIG. 5A is a block diagram showing a configuration of a video signal processing circuit forming the first embodiment;

FIG. 5B is a circuit diagram showing a configuration of an analog clamp circuit in FIG. 5A;

FIG. 5C is a circuit diagram showing a configuration of a digital clamp circuit in FIG. 5A;

FIGS. 7A to 7F are timing charts of driving of a CCD in a special light mode according to the first embodiment;

FIGS. 8A to 8F are timing charts of driving of a CCD in a normal light mode according to the first embodiment;

FIG. 14A is a block diagram showing a configuration of a video signal processing circuit in the second embodiment of the present invention;

FIG. 14B is an illustration of digital image correction on an image with a white spot by pixels around;

FIG. 14C is a diagram showing a configuration of a white spot correction circuit;

FIGS. 15A to 15E are diagrams showing a configuration or the like of a charge-coupled device solid image-pickup device in the precedence example.

DETAILED DESCRIPTION OF THE PREFERRED EMBODIMENT(S)

The embodiments of the present invention will be described below with reference to the drawings.

First Embodiment

The first embodiment of the present invention will be described with reference to FIG. 1 to FIG. 13.

First, a configuration of an endoscope device with the embodiment will be described.

Figure 1:
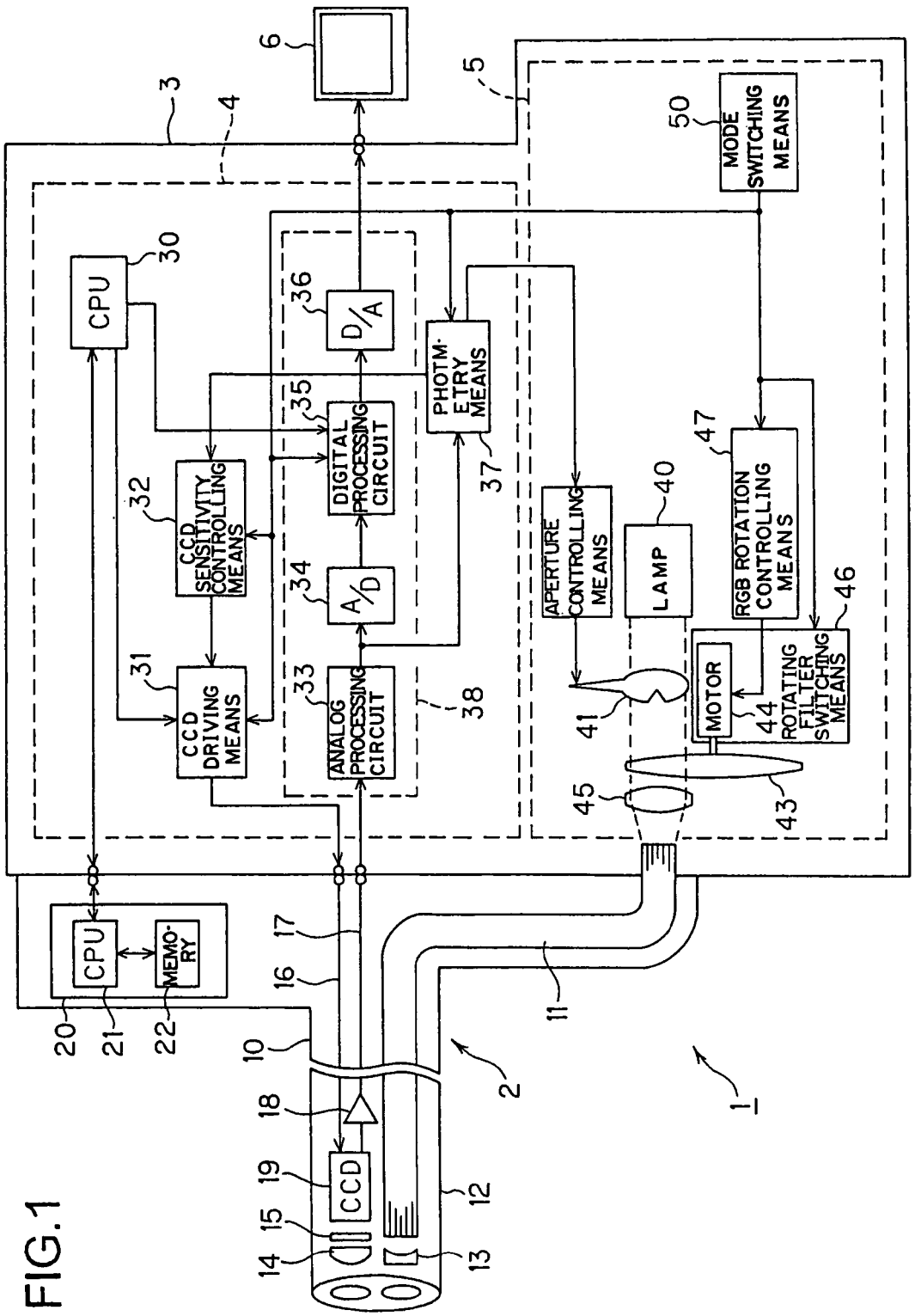
FIG. 1 is a block diagram showing an outlined configuration of an endoscope device with a first embodiment of the present invention.

As shown in FIG. 1, an endoscope device 1 with the first embodiment comprises a medical electronic endoscope (hereinafter referred to as an endoscope for short) 2 which is inserted in a body cavity of a patient, a processor 3 which is detachably connected to the endoscope 2 for supplying the endoscope 2 with an illumination light and which performs signal processing on an image-pickup device, and a monitor 6 for displaying an endoscope image.

The processor 3 includes an endoscope signal processing device (hereinafter, simply referred to as a signal processing device for short) 4 and a light source device 5 of the first embodiment. The light source device 5 may be provided independent of the processor 3.

To an image output terminal of the processor 3, the monitor 6 is connected. A video signal generated by image processing is inputted from a signal processing device 4 of the processor 3 to the monitor 6 and the monitor 6 displays an endoscope image corresponding to the video signal.

The endoscope 2 has an elongate inserting section 10 which is inserted into a body cavity of a patient.

Here, the inserting section 10 comprises a flexible member when it is used for alimentary canals, a bronchial, a head and a neck (throat) or a bladder, but comprises a rigid member when it is used for an abdominal cavity, a chest cavity or a womb. A light guide 11 for transmitting illumination is inserted into the inserting section 10. The back end of the light guide 11 is detachably connected to the light source device 5 of the processor 3 and supplied with illumination light from the light source device 5.

The illumination light supplied to the back end of the light guide 11 is transmitted to the distal-end surface by the light guide 11. The distal-end surface of the light guide 11 is placed in the distal portion 12 of the inserting section 10 and emitted on a subject side such as an affected area in a body cavity from the distal-end surface of the light guide 11 via an illumination lens 13 attached on an illumination window which is facing opposite.

The distal portion 12 is provided with an observation window adjacent to the illumination window. The observation window is attached with an objective lens 14 on which a subject is imaged. The charge coupled device (abbreviated as CCD) 19 is placed in the imaging place. In a light channel between the objective lens 14 and the CCD 19, an excitation light cut filter 15 for cutting an excitation light which is used in fluorescent observation is placed.

The excitation light cut filter 15 placed on the front side of the CCD 19 transmits only a particular wavelength band. In the embodiment, the excitation light cut filter 15 has a spectrum characteristic which transmits self fluorescence (about wavelength of 500 nm or more) emitted from a tissue from a living body but does not transmit excitation light.

A reflection light and a self fluorescence from a subject is imaged on a photo-receiving surface of the CCD 19 via the objective lens 14 and the excitation light cut filter 15.

The CCD 19 placed in the distal portion 12 of the inserting section 10 is connected to a CCD driving signal line 16 which is inserted into the inserting section 10 and also connected to a CCD output signal line 17 via a preamp 18 placed near the CCD 19.

The CCD 19 placed at the distal portion 12 of the inserting section 10 is an image sensor provided at an imaging place on the objective lens 14. Although it is provided as being seen straight in FIG. 1, it can be provided as being seen oblique or from a side.

The CCD 19 is connected to a CCD driving means 31 of the signal processing device 4 in the processor 3 via the driving signal line 16. The CCD 19 performs electronic shutter control, accumulation of signal charges, sensitivity control and reading out with a driving signal generated by the CCD driving means 31.

A subject imaged on a photo-receiving surface of the CCD 19 by the objective lens 14 and the excitation light cut filter 15 is transferred and outputted from an output amplifier after being subject to photoelectric conversion at each pixel of the CCD 19. The output signal from the CCD 19 is amplified by the preamp 18, then passes through a CCD output signal line 17 which is inserted into the inserting section 10, and inputted into an analog processing circuit (or an analog signal processing section) 33 which forms a video signal processing circuit 38 of the signal processing device 4 in the processor 3, to which the connector section is detachably connected, from a connector section.

The endoscope 2 is mounted with a storage device 20 to a connector section or the like at a base-end terminal side of the inserting section 10. The storage device 20 comprises a CPU 21 and memory 22, for example.

The memory 22 uses non-volatile EEPROM or the like and can store data.

The CPU 21 controls reading-out and writing-in of data from/to the memory 22, and also controls transmitting/receiving (communication) of data with the CPU 30 in the processor 3.

The memory 22 stores an accumulation time (electronic shutter speed) with three wavelengths of R, G, and B in a normal light mode, and an accumulation time (electronic shutter speed) with three wavelengths of Ex1 (fluorescent), Ex2 (green reflection light), and Ex3 (red reflection light) in a special light mode (fluorescent observation). The memory 22 may store a charge clear time, accumulation time ratio of three wavelengths of R, G, B, or Ex1, Ex2, and Ex3, instead of an accumulation time.

In the memory 22, the accumulation time of a wavelength of fluorescent is set longer than the accumulation time of a two wavelengths of a reflected light for a wavelength of fluorescent light wavelength and two wavelengths of a reflected light.

An accumulation time of three wavelengths of R, G, and B in a normal light mode to be stored in the memory 22 is set shorter than that in an endoscope mounted with a CCD that is not a sensitivity variable CCD such as the CCD 19.

As an accumulation time of three wavelengths in a special light mode to be stored in the memory 22, optimum accumulation time is set for kinds of a plurality of endoscopes (for a bronchial, upper alimentary canals, lower alimentary canals, a head and a neck (throat), a bladder or the like). This is because a fluorescent intensity and a reflected light intensity obtained for each part are different, and an accumulation time is set among three wavelengths so that they have the intensity in an equivalent level.

The memory 22 stores other data relating to an endoscope other than data on the accumulation time.

As data to be stored in this case, a name of an endoscope model (type), an endoscope serial number, a white balance set value (for fluorescent, for special light (fluorescent observation)), the number of times that an endoscope is connected to a processor and powered on, information on an clamp channel of an endoscope, outside diameter data at the distal portion of an endoscope, outside diameter data of the inserting section of an endoscope or the like are known.

In the embodiment, the signal processing device 4 comprises a CPU 30, CCD driving means 31, CCD sensitivity controlling means 32, an analog processing circuit 33, an analog/digital converter (herein after referred to as A/D converter) 34, a digital processing circuit 35, a digital/analog converter (hereinafter referred to as D/A converter) 36, and photometry means 37.

The light source device 5 comprises a lamp 40, an aperture 41, aperture controlling means 42, an RGB rotating filter 43, a motor 44, a condenser 45, rotating filter switching means 46, RGB rotating filter controlling means 47, and mode switching means 50.

When the endoscope 2 is connected to the processor 3, the CPU 30 performs read-out control on various types of data stored in the memory 22 via the CPU 21. In this case, the various data stored in the memory 22 is outputted to the CPU 30 via the CPU 21 and the various types of data are read out by the CPU 30.

The CPU 30 outputs accumulation time data of three wavelengths, in the normal light mode and the special light mode (fluorescent observation), obtained from the memory 22 to the CCD driving means 31.

The CPU 30 outputs a name of an endoscope model, serial No., or a white balance set value (for a normal light, for a special light) or the like to the digital processing circuit 35.

Next, the CCD 19 will be described in detail.

In the embodiment, as a CCD 19, a CCD which has variable sensitivity by using a collision ionization phenomenon described, for example, in U.S. Pat. No. 5,337,340, "Charge Multiplying Detector (CMD) suitable for small pixel CCD image sensors".

The CCD 19 is provided with a charge amplifying section between a horizontal transfer channel and an output amplifier in a CCD or in each pixel. When a high electric field pulse is applied to the charge amplifying section from a processor, a signal charge obtains energy from a strong electric field and collides against an electron in a valence electron band, and a signal charge (secondary electron) is generated anew by collision ionization.

For example, when an avalanche effect is used, secondary electron generation occurs in a chain reaction with a pulse applied. When collision ionization is used, only a pair of an electron with a positive hole is generated by application of a pulse which is in a relatively low voltage.

In the CCD 19, when the charge amplifier section is provided in the previous stage of an output amplifier, the number of signal charges can be arbitrary amplified with a voltage value (amplitude) of a pulse to be applied being controlled.

On the other hand, if a charge amplifier section is provided in each pixel, the number of signal charges can be arbitrary amplified with a voltage value (amplitude) of a pulse or the number of pulses to be applied being controlled.

Figure 2:
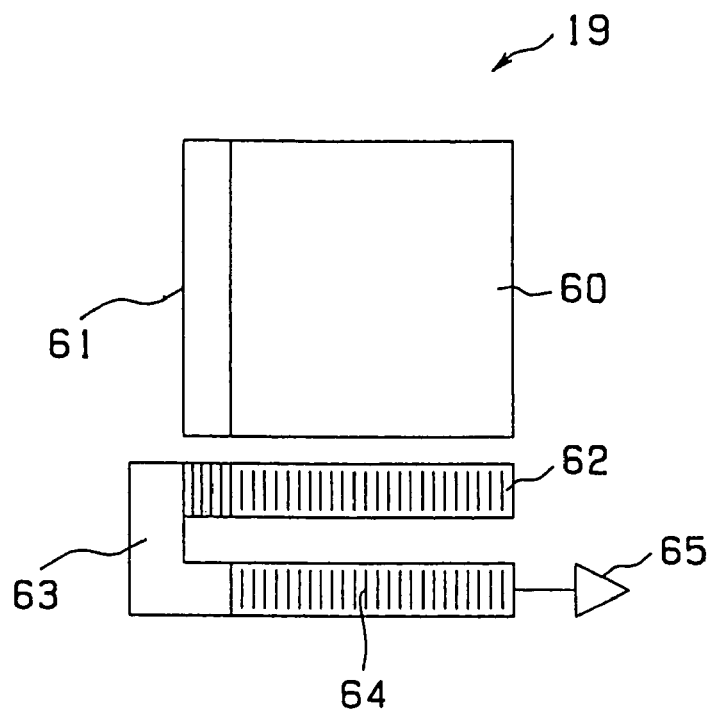
FIG. 2 is a block diagram showing a configuration of a charge-coupled device solid image-pickup device according to the first embodiment.

Then, in the case of the embodiment, an FFT (Full Frame Transfer) type monochrome CCD with a charge amplifying section mounted between a horizontal transfer channel and an output amplifier is used as a CCD 19 as shown in FIG. 2.

The CCD 19 has an image area 60, an OB (Optical Black) area 61, a horizontal transfer channel 62, a dummy section 63, a charge amplifying section 64, and an output amplifier section 65. The charge amplifying section 64 comprises the number of cells which is the same or double of the number of cells of the horizontal transfer channel 62.

The signal charges which are photoelectrically converted and generated in each pixel of the image area 60 are transferred to the horizontal transfer channel 62 for each horizontal line by vertical transfer pulses ΦP1, ΦP2, and transferred to the dummy section 63 and the charge amplifying section 64 from the horizontal transfer channel 62 by horizontal transfer pulses ΦS1, ΦS2. When a sensitivity control pulse φCMD is applied to each cell of the charge amplifying section 64 comprising a plurality of cells, a signal charge is amplified in order stage by stage as each cell is transferred, and transferred to the output amplifier 65 in order. The output amplifier 65 converts the signal charge from the charge amplifying section 64 into voltage and outputs it.

The OB area 61 comprises a photo diode which is the same as the one for the image area 60, and adapted to be used for shielding a light on its photosensitive surface by metal, and correcting a change of the black level by temperature or an amplification ratio.

The dummy section 63 is used when a signal is transferred from a pixel in the image area 60 and the OB area 61. The dummy section 63 comprises a device which is the same as the one for the horizontal transfer section 62. The dummy section 63 has no defective pixel where it exists in a pixel of a photodiode in the image area 60 or the OB section 61. The dummy section 63 has little temperature characteristic.

For that reason, by performing analog clamp processing which is necessary in an analog circuit for performing analog processing within a signal outputting time period of the dummy section 63 to be mentioned later, a signal with closely equivalent to an analog clamp in the original OB area 61 where no white spot is present is obtained.

Figure 3:
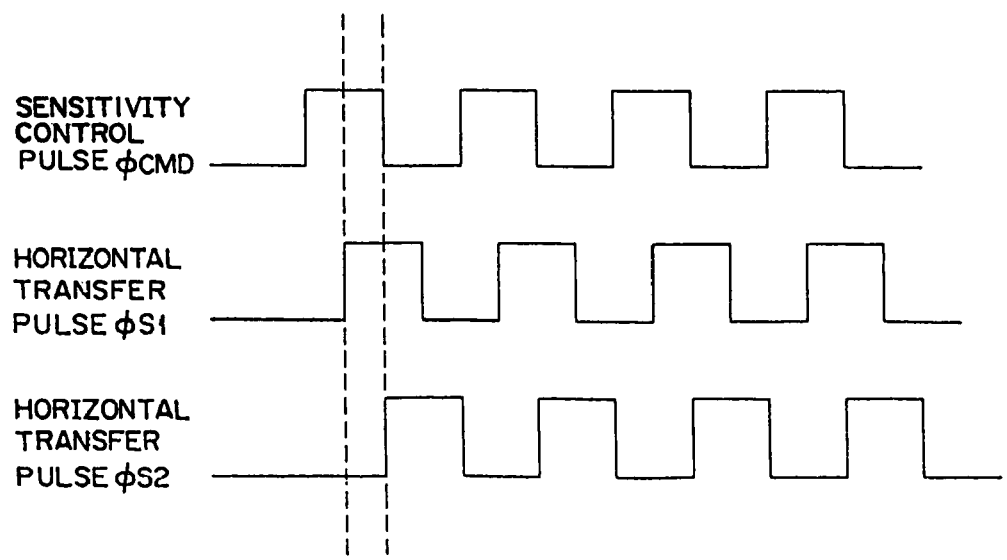
FIG. 3 is a timing chart of various pulses ΦCMD, ΦS1, ΦS2 according to the first embodiment.

In the CCD 19 used in the embodiment, phases of a sensitivity control pulse φCMD and horizontal transfer pulses φS1, φS2 are as shown in FIG. 3. That is to say, the sensitivity control pulse φCMD of FIG. 3 rises before the horizontal transfer pulse φS1 shown in FIG. 3 rises, and the φCMD falls before the horizontal transfer pulse φS1 falls. The sensitivity control pulse φCMD in FIG. 3 forms an inverted-phase to the horizontal transfer pulse φS2 shown in FIG. 3.

Figure 4:
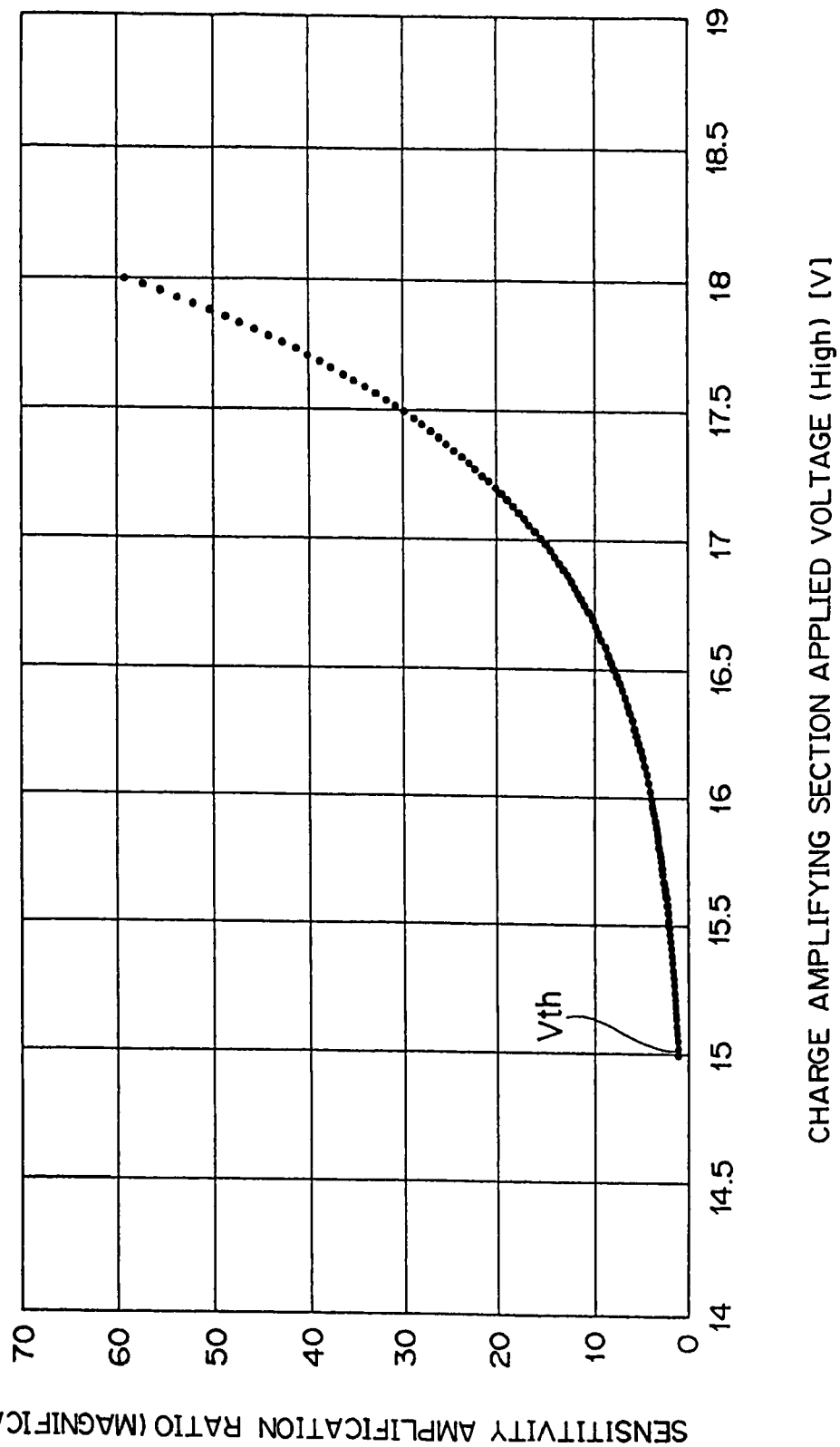
FIG. 4 is an illustration showing relationship between a CMD applied voltage and a CMD amplification ratio according to the first embodiment.

A sensitivity amplification ratio obtained at the charge amplifying section 64 becomes variable by varying a size of a voltage value (amplitude) of the sensitivity control pulse φCMD sent from the CCD driving means 31 to the charge amplifying section 64. The sensitivity amplification ratio obtained at the charge amplifying section 64 has a characteristic such that charge amplifying starts when it exceeds a certain threshold Vth with respect to a voltage applied to the charge amplifying section 64 as shown in FIG. 4, and the sensitivity amplification ratio exponentially increases as the sensitivity amplification ratio further increases.

When the sensitivity control pulse φCMD is 0(V) to threshold Vth, a signal charge is not amplified and only transferred to the charge amplifying section 64. A threshold to start a charge amplifying and steepness of a sensitivity amplification ratio against an applied voltage is designed to be variable.

The CCD 19 is provided with an electronic shutter function. An operational principle of the electronic shutter is, similarly to a general CCD, in a substrate ejecting form, which uses a change in an overflow characteristic which varies due to a voltage value (amplitude) of a pulse applied to an Over Flow Drain, for example.

In a time period of a pulse φOFD for an electronic shutter to be applied to the Over Flow Drain is being inputted into the CCD 19 (H level), a signal charge (including a noise charge) in a pixel of the CCD 19 is ejected to a substrate and the signal charge is not accumulated in the pixel of the CCD 19.

In a time period of the electronic shutter pulse φOFD is not being inputted into the CCD 19, a signal charge is accumulated in a pixel of the CCD 19.

As any value can be set as a pulse width or the number of pulses of φOFD, an accumulating time of a signal charge of the CCD 19 can be controlled by any time.

FIG. 5A shows a configuration of the video signal processing circuit 38 which performs reproducing of a direct current, processing of extracting a signal component, or the like, on a signal which is photoelectrically converted by the image area 60 from a signal outputted from the CCD 19 in the signal processing device 4 of the embodiment.

Although an output signal of the OB area is clamped and reproducing of a direct current is performed for reproducing the black level in a signal which is photoelectrically converted in output signals of a solid image-pickup device in the precedence example, the embodiment has a signal level near the signal level in the OB area to be described later and clamps, as a reference signal of the black level, a signal of the dummy section 63 which has no white spot nor an photoelectric conversion function.

Figure 6A:
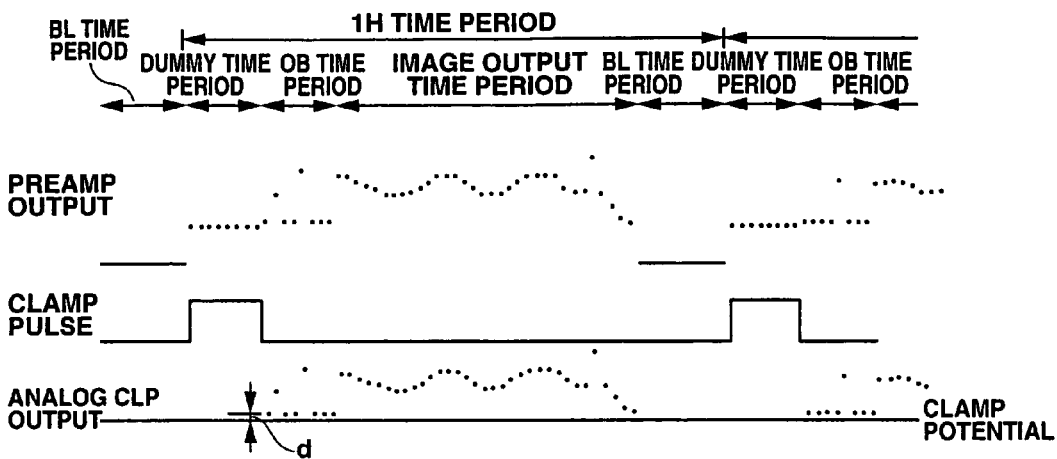
FIG. 6A is a timing chart showing detailed operation to an analog clamp circuit.

The CCD output signal which is amplified via a preamp 18 from the CCD 19 is inputted into a first analog clamp circuit (a first signal clamp section; referred to as an analog CLP for short in the figure) 71, and clamped in a signal outputting time period (in FIG. 6A, a dummy time period) of the dummy section 63 for each horizontal time period (in FIG. 6A, shown as 1H time period) so that a signal level is adjusted so as to fit in the input range of a CDS circuit (in FIG. 5 and the like, CDS IC) 72 which performs correlation double sampling (abbreviated as CDS).

The CCD outputted signal inputted into the CDS circuit 72 is inputted into the A/D converter (specifically A/D IC in FIG. 5A) 34 that performs A/D conversion after base band signals which are the CCD outputted signal components extracted are generated, and the signals are inputted into a second analog clamp circuit (first signal clamp section) 73 and clamped at the dummy section 63 for each horizontal line.

A digital signal converted from an analog signal by the A/D converter 34 is inputted into a digital clamp circuit (second signal clamp section or OB level correction processing circuit) 74, and subject to processing for digitally clamping with a signal in the OB area 61 (in other words, signal level correcting processing to make an average value of the signal levels of all pixels in the OB area 61 the black level), then, inputted into a post-digital processing circuit 75.

The post-digital processing circuit 75 performs signal processing such as white balance processing, color converting processing, electronic zoom processing, gamma converting processing, image enhancing processing or the like on an inputted signal, then performs simultaneous processing and generates a digital video signal and outputs it to D/A converter 36.

The white balance processing and the color converting processing differ for observation modes of a normal light mode and a special light mode (fluorescent observation) to be described later. The post digital processing circuit 75 performs different kinds of processing according to a mode switching signal from the mode switching means 50.

The analog video signal converted by the D/A converter 36 is outputted to a monitor 6. The video signal outputted from the D/A converter 36 is also outputted to a display device and a storage device which are peripheral appliances (not shown).

The first analog clamp circuit 71 clamps with a clamp pulse in a signal outputting time period of the dummy section 63 for each horizontal time period, and sets its average level to a lower limit of an input range of the CDS IC 72. That is to say, a signal in the dummy section 63 is used for a reference signal of the black level, clamped by a clamp pulse in an output time period of the signal so that an analog black level is reproduced.

A configuration of the first analog clamp circuit 71 is shown in FIG. 5B. The output signal from the preamp 18 is inputted into the CDS IC 72 through a condenser 81 which blocks a direct current portion, and applied to a collector of a clamp transistor 82.

To the base of the clamp transistor 82, a clamp pulse which is synchronized with a signal outputting time period of the dummy section 63 is applied. To an emitter of the transistor 82, a reference voltage set for a lower limit level of the input range of the CD IC 72 is applied. When the clamp pulse is applied to the base, an output terminal of the analog clamp circuit 71, i.e., a potential of the collector is clamped to a potential of the reference voltage.

A configuration of the second analog clamp circuit 73 is the same as the configuration of the first analog clamp circuit 71, except that the reference voltage is set according to the input range of the A/D converter 34.

FIG. 5C shows a configuration of the digital clamp circuit 74. A digital signal inputted from the A/D converter 34 is inputted into a subtracter 83 and also inputted into an adder 84. To the adder 84, an input signal is added during a time period of the OB clamp pulse being applied. As the OB clamp pulse is generated by a pulse width of the number of horizontal pixels in the OB area 61 and by the number of the pulse in the pulse width in the number of vertical pixels, the adder 84 adds (adds up) signals of the entire pixels in the OB area 61.

The output signal from the adder 84 is inputted into a divider 85, which divides the output signal from the adder 84 by the number of pixels in the OB area 61, and calculates an average value of the signal level of the OB area 61.

The output signals from the divider 85 is inputted in the subtracter 83, where the average value of a signal level of the entire pixels in the OB area 61 is subtracted from the output signals from the A/D converter 34 so that the average value of the signal level of the entire pixels in the OB area 61 becomes the black level. That is to say, the signal level outputted from the subtracter 83 is adjusted (direct current resumption) in level so that the average level in the OB area 61 becomes the black level.

FIG. 6A is a timing diagram showing a detailed processing operation of the first analog clamp circuit 71 of FIG. 5B.

As to signals inputted from the preamp 18 to the first analog clamp circuit 71 (preamp output in FIG. 5B), collector emitters of a transistor 82 are turned ON (conducted there between) when a clamp pulse is set to "H" level in a dummy time period following to a horizontal blanking time period (BL time period in FIG. 6A).

When the transistor 82 is turned ON, the signal level outputted from the first analog clamp circuit 71 is clamped to a reference voltage which is set so that the direct current level of the signal level of the dummy section 63 matches to the input range of the CDS IC72, and becomes a signal whose direct current is reproduced.

In such a case, as the dummy section 63 has no photodiode (photo-receiving section), no defective pixel such as a white spot is present as mentioned above, and little depends on temperature. Therefore, a case where a clamp level to be clamped is shifted up due to a white spot in the case of clamping in the OB area in the precedence example does not occur.

However, only with this a change in temperature or an amplification ratio is not corrected. Thus, it is clamped slightly lower than the original black level by a small level difference d, unlike the original signal level (except for a white spot) in the OB area 61 as shown in FIG. 6A.

As it is clamped slightly lower than the signal level in the original OB area 61 like that, an influence can be virtually eliminated when the digital clamp circuit 74 shown in FIG. 5A or 5C performs digital clamp processing using the entire OB area 61.

That is to say, if OB clamp is performed using the entire pixels in the horizontal and the vertical directions in the OB area 61, the average value in using the entire pixels in the OB area 61 can be made small enough even if a white spot is present.

Illustrating that with a specific example, when the number of horizontal and vertical pixels of the image area 60 is 400×400, for example, the OB area 61 also has 400 horizontal lines formed (in a vertical direction), influence of a white spot in horizontal lines in which the white spots are present increases due to the small number of pixels in the horizontal line, but the influence can be reduced to around 1/400 or lower by averaging it by the entire pixels in 400 lines.

The influence of a white spot can be reduced to some extent even if it is digital clamped by using only a part of pixels in the OB area 61 instead of using the entire pixels. That is to say, the influence of a white spot can be reduced compared to the precedence example, even by OB clamping in a part of two-dimensional area (in other words, the number of pixels by a plurality of horizontal lines in the OB area 61) in the entire of the two dimensional area of the OB area 61.

Figure 6B:
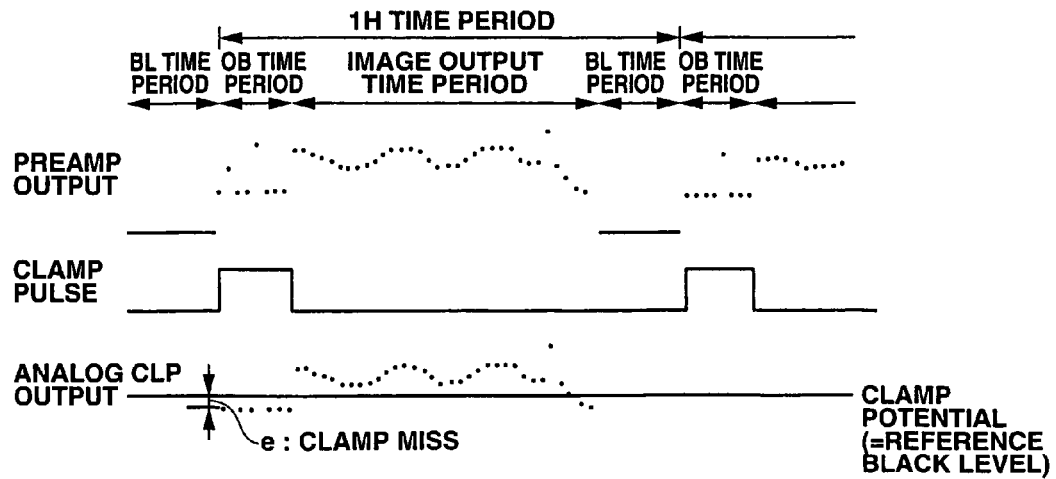
FIG. 6B is a timing chart showing detailed operation to an analog clamp circuit in the precedence example.

To the contrary, illustrating the case of the precedence example, as analog clamp is performed in the horizontal pixel lines of the OB area 61 in the precedence example and the number of pixels in the horizontal line is small, the analog clamp processing in the case of the horizontal line becomes as shown in FIG. 6B even with a single white spot.

In the case of the precedence example, as it is performed in the OB area 61 instead of in the dummy section 63 which has no function of photoelectrically converting a clamp pulse and no defective pixels, if a white spot is in the OB area 61 as shown in FIG. 6B, the direct current level in the OB area 61 is shifted higher than the original direct current level (in the state where no white spot is present) due to the white spot.

As shown in FIG. 6B, a clamp miss with a level difference occurs as shown by a code e, for example. The level difference e sets a clamp potential at a value higher than the level of the original OB area 61. That is to say, as it is set to the black level a value higher than an actual black level, the part higher than the black level is displayed as the black level in black lines on an image, which leads degradation of an image quality.

To the contrary, the embodiment is characterized by being adapted to generate a clamped signal when a signal from the dummy section 63, which is unaffected by a white spot (or has no defective pixel such as a white spot) (in the OB area 61) and outputs a signal of a value near the signal level in the OB area 61, is clamped as a reference signal (in place of a signal for the black level in the OB area 61) so as not to subject to an influence of the white spot (influence to lower an image quality in black lines).

FIGS. 7A to 7F are timing charts showing driving signals and output signals from the CCD 19 by a single wavelength of three wavelengths in a special light mode; with FIG. 7A indicating operation of the RGB rotating filter 43 in a special light mode, FIG. 7B indicating vertical transfer pulses φP1, ΦP2 in a special light mode, FIG. 7C indicating a sensitivity control pulse φCMD in a special light mode, FIG. 7D indicating a horizontal transfer pulses ΦS1, ΦS2 in a special light mode, FIG. 7E indicating an electronic shutter pulse φOFD in a special light mode, and FIG. 7F indicating an output signal from the CCD 19 in a special light mode, respectively.

FIGS. 8A to 8F show timing charts of driving signals and output signals from the CCD 19 by a single wavelength of three wavelengths in a normal light mode; with FIG. 8A indicating operation of the RGB rotating filter 43 in a normal light mode, FIG. 8B indicating vertical transfer pulses φP1, ΦP2 in a normal light mode, FIG. 8C indicating a sensitivity control pulse φCMD in a normal light mode, FIG. 8D indicating a horizontal transfer pulses ΦS1, ΦS2 in a normal light mode, FIG. 8E indicating an electronic shutter pulse φOFD in a normal light mode, and FIG. 8F indicating an output signal from the CCD 19 in a normal light mode, respectively.

The CCD driving means 31 outputs the vertical transfer pulses φP1, ΦP2, the sensitivity control pulse φCMD, the horizontal transfer pulses ΦS1, ΦS2, and the electronic shutter pulse φOFD to the CCD 19 as driving signals.

Here, in FIGS. 7A to 7F and FIGS. 8A to 8F, a single cycle indicates a cycle for a wavelength of three wavelengths and indicates operation for ⅓ rotation of the RGB rotating filter 43.

Time periods TE (special light mode), TE' (normal light mode) are exposure time periods. The CCD 19 can accumulate lights incident from a subject to the CCD 19 photo-receiving surface in the exposure time period as signal charges by photoelectrically converting the lights.

The time periods TD (special light mode) and TD' (normal light mode) are time periods for transferring signal charges accumulated in the image area 60 in the time periods TE, TE' respectively to the horizontal transfer channel 62 by the vertical transfer pulse φP1, ΦP2 for each horizontal line, transferring them to the dummy section 63, the charge amplifying section 64, and output amplifier section 65 in order by the horizontal transfer pulses ΦS1, ΦP2, and converting from charges to voltages at the output amplifier section 65 and outputting them.

In the special light mode, to the RGB rotating filer 43, the exposure time period TE and the light-shield time period TD shown in FIG. 7A are set in a single cycle.

The electronic shutter pulse φOFD shown in FIG. 7E becomes a high level pulse time period TC for performing charge clearance of a pixel of the CCD 19 at the beginning of the exposure time period TE shown in FIG. 7A, then falls to a low level and becomes a charge accumulation time period TA for causing pixels in the CCD 19 to accumulate charges.

In the light-shielding time period TD shown in FIG. 7A, i.e., a reading-out time period TD of the CCD 19, the CCD driving means 31 outputs the vertical transfer pulses φP1, ΦP2 shown in FIG. 7B, the sensitivity control pulse φCMD shown in FIG. 7C, and the horizontal transfer pulses ΦS1, ΦS2 shown in FIG. 7D, which causes the CCD 19 to be read out and gives an output signal from the CCD 19 as shown in FIG. 7F.

Here, the CCD driving means 31 makes a voltage value (amplitude) variable based on data supplied from the CCD sensitivity controlling means 32 as to the sensitivity control pulse φCMD shown in FIG. 7C. The CCD driving means 31 outputs to the CCD 19 the sensitivity control pulse φCMD shown in FIG. 7C with phase relationship between the horizontal transfer pulses ΦS1, ΦS2 shown in FIG. 7D.

That makes the CCD driving means 31 control the CCD 19 so as to change a voltage value (amplitude) of the sensitivity control pulse φCMD to be applied to the charge amplifying section 64 and to obtain a desired sensitivity amplification ratio, in the special light mode.

In the normal light mode, an exposure time period TE' and a light-shield time period TD' shown in FIG. 8A in a cycle is set in the RGB rotating filter 43.

The electronic shutter pulse φOFD shown in FIG. 8E becomes a high level pulse time period TC' for performing charge clearance on a pixel of the CCD 19 at the beginning of the exposure time period TE' shown in FIG. 8A, then falls to a low level, and becomes a charge accumulation time period TA' for causing pixels in the CCD 19 to accumulate charges.

In the light-shielding time period TD' shown in FIG. 8A, i.e., a reading-out time period TD' of the CCD 19, the CCD driving means 31 outputs the vertical transfer pulses φP1, φP2 shown in FIG. 8B, the horizontal transfer pulses ΦS1, ΦS2 shown in FIG. 8D, which causes reading-out from the CCD 19 and outputs an output signal from the CCD 19 shown in FIG. 8F.

Here, the CCD driving means 31 does not output the sensitivity control pulse φCMD as shown in FIG. 8C in the normal light mode. Alternatively, it may output the sensitivity control pulse ΦCMD of an electronic value of Vth or lower.

That makes a charge amplifying not to be performed in the charge amplifying section 64 in the normal light mode and the sensitivity amplification ratio is one time.

If a usual endoscope to which no sensitivity variable CCD as used in the CCD 19 is mounted is connected to the processor 3, the CCD driving means 31 performs operation in the normal light mode as shown in FIGS. 8A to 8F.

The electronic shutter pulse φOFD shown in FIG. 7E and FIG. 8E is a pulse for emitting charges accumulated in each pixel to a substrate and is outputted by any pulse width or in the number of a plurality of pulses during the time period from a start of an exposure time period to an end of the time period (start of light-shielding time period).

The time periods TE, TE' shown in FIGS. 7A to 7F and FIGS. 8A to 8F are time periods which can accumulate subject images in the image area 60 of the CCD 19, but signal charges are not accumulated for the time periods TC, TC' during which the electronic shutter pulse φOFD shown in FIG. 7E and FIG. 8E is outputted. When the electronic shutter pulse φOFD shown in FIG. 7E and FIG. 8E is no longer outputted, signal charges are started to be accumulated in each pixel in the CCD 19. The time period TA from a start of accumulation to a start of a light-shielding time period (=time period TE-time period TC) (special light mode) and TA' (=time period TE'-time period TC') (normal light mode) are practical accumulation times.

For the electronic shutter pulse φOFD of each wavelength, a pulse width or the number of pulses based on an accumulation time of each wavelength from the CPU 30 is outputted to the CCD 19.

For example, assuming that three wavelengths in a special light mode are Ex1, Ex2, and Ex3, and when accumulation times among three wavelengths in a special light mode stored in the memory 22 are TA(Ex1)=TE, TA(Ex2)=0.2*TE, TA(Ex3)=0.1*TE, the data is supplied to the CCD driving means 31 via the CPU30, and a pulse width of the electronic shutter pulse φOFD of a charge clear outputted from the CCD driving means 31 to the CCD 19 becomes OFD(Ex1)=0*TE, OFD(Ex2)=0.8*TE, OFD(Ex3)=0.9*TE.

If accumulation times among three wavelengths in a normal light mode stored in the memory 22 is, for example, TA' (R)=0.7*TE', TA' (G)=0.7*TE', TA' (B)=0.7*TE', the data is supplied to the CCD driving means 31 via the CPU 30, and the electronic shutter pulse φOFD is outputted from the CCD driving means 31 to the CCD 19 based on the data. The pulse width of the electronic shutter pulse φOFD which performs charge clear becomes OFD(R)=OFD(G)=OFD(B)=0.3*TE'.

As mentioned above, for a signal outputted from the CCD 19, a digital video signal is generated by the video signal processing circuit 38, converted into an analog video signal by the D/A converter 36, and then outputted to the monitor 6 or the like.

In such a case, white balance processing or color converting processing processed in the digital processing circuit 35 in the video signal processing circuit 38 are different for respective observation modes in the normal light mode and the special light mode (fluorescent observation), and the digital processing circuit 35 performs different processing according to mode switching signals from the mode switching means 50.

For the color converting processing in the special light mode (fluorescent observation), a fluorescent wavelength and two wavelengths of a reflected light are multiplied by a certain matrix coefficient, and a combined image of a fluorescent wavelength and two wavelengths of a reflected light are built.

In the white balance processing, a set value stored in the memory 22 is inputted in the digital processing circuit 35 via the CPU 30 and white balances different between the normal light mode and the special light mode (fluorescent observation) are set.

To the photometry means 37, a video signal from the analog processing circuit 33 is inputted and screen average values of brightness of three wavelengths in the normal light mode and the special light mode (fluorescent observation) are calculated.

Here, in the photometry means 37, a calculation method of a screen average value performs different operation in the normal light mode and the special light mode (fluorescent observation) according to the mode switching signal from the mode switching means 50.

In the normal light mode, the photometry mode 37 calculates brightness signal from the screen average value as to three wavelengths of R, G, and B and outputs it to the aperture controlling means 42 of the light source device 5.

In the special light mode (fluorescent observation), the photometry means 37 calculates screen average value as to three wavelengths of Ex1, Ex2, Ex3, generates a screen average value of a combined image comprising a fluorescent wavelength and two wavelengths of a reflected light, and outputs it to the CCD sensitivity controlling means 32 and the aperture controlling means 42.

The CCD sensitivity controlling means 32 performs AGC (Auto Gain Control) by controlling the charge amplifying section 64 provided to the CCD 19 in the special light mode. The CCD sensitivity controlling means 32 addresses a change in a intensity of a subject incident on a photo-receiving surface of the CCD 19, and controls the sensitivity amplification ratio of the charge amplifying section 64 of the CCD 19 so that an average of the signal levels output from the CCD 19 becomes a desired value.

To the CCD sensitivity controlling means 32, a screen average value of the combined image of the fluorescent image and the reflected light is inputted from the photometry means 37, and the screen average value and the monitor brightness value (target value) which is set by the operator are compared.

The operator can set a target value of brightness on a monitor screen from the brightness setting means provided to the light source device 5 or the signal processing device 4 (not shown). The CCD sensitivity controlling means 32 compares the screen average value and the brightness set value (target value), calculates a voltage value (amplitude) of the sensitivity control pulse ΦCMD to be outputted from the CCD driving means 31 to the charge amplifying section 64 of the CCD 19 based on the compared result (relationship of big and small), and outputs it to the CCD driving means 31.

The AGC controlling method of the CCD sensitivity controlling means 32 will be described below.

Relationship between the voltage value of the sensitivity control pulse ΦCMD of the charge amplifying section 64 and the sensitivity amplification ratio shown in FIG. 4 will be approximated by the expression below.

$$M(V) = C \cdot \mathrm{Exp}\{\alpha(V-Vth)\} \quad (1)$$

M(V) is the sensitivity amplification ratio when the voltage value (amplitude) of the sensitivity control pulse ΦCMD is V(v), Vth is a threshold value with which the charge amplification starts, C, α, Vth are constants variable in design and unique to the device.

When a subject image with a certain intensity is captured by a CCD, the CCD sensitivity controlling means 32 changes (increases or decreases) the size of a voltage value (amplitude) of the sensitivity control pulse φCMD so that a screen average value of the combined fluorescent image and monitor brightness and a target value set by an operator match corresponding to a change of intensity in fluorescence and reflected light from a subject, by using the fact that the screen average value of an image exponentially changes due to increase or decrease of a voltage value of the sensitivity control pulse φCMD. The CCD sensitivity controlling means 32 controls the CCD driving means 31 so that an applied voltage becomes 0(V) when the voltage value of the sensitivity control pulse φCMD is the threshold or lower.

Figure 9:
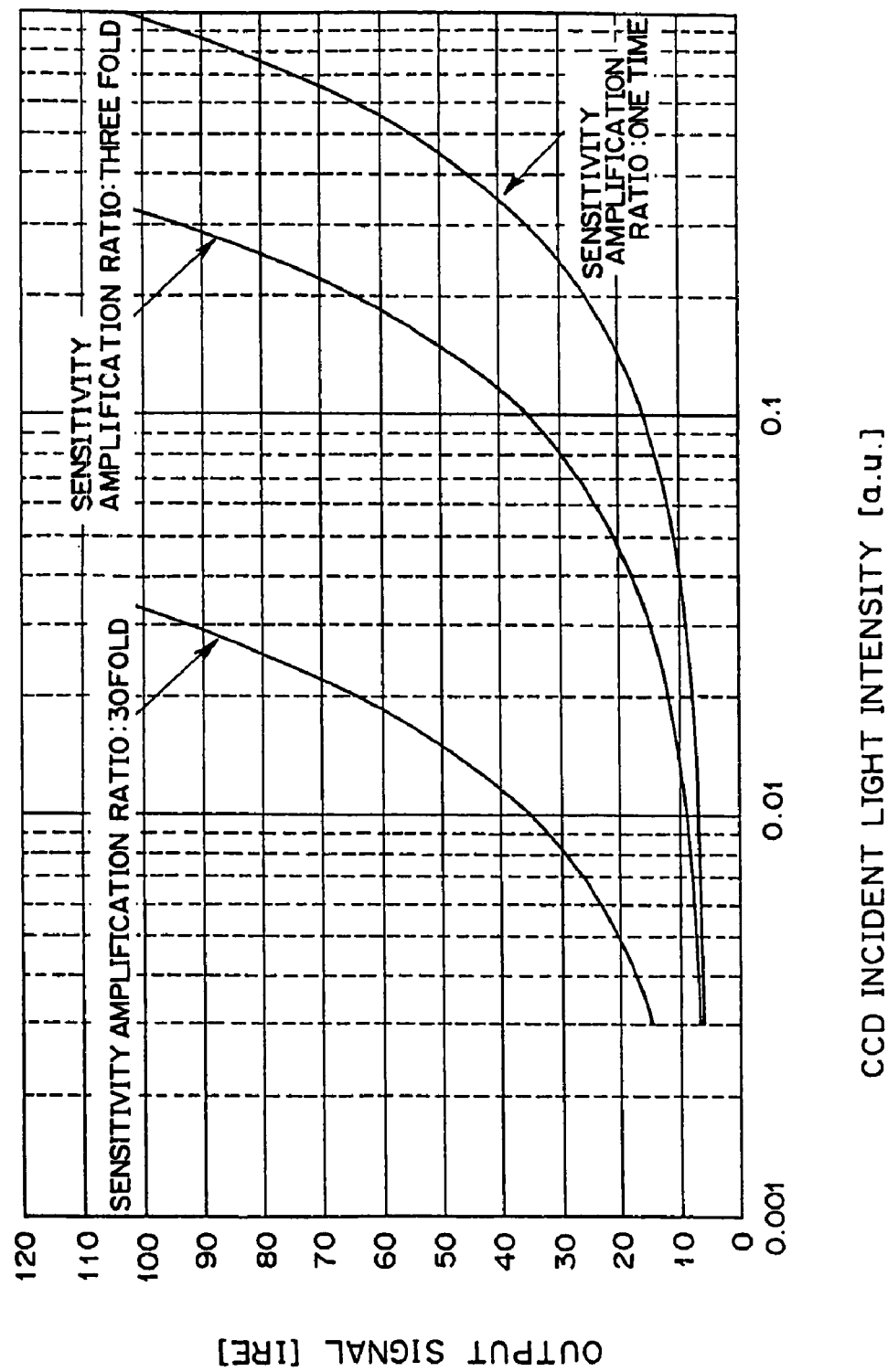
FIG. 9 is a graph showing a CCD sensitivity characteristic (monitor output signal) according to the first embodiment.
Figure 10:
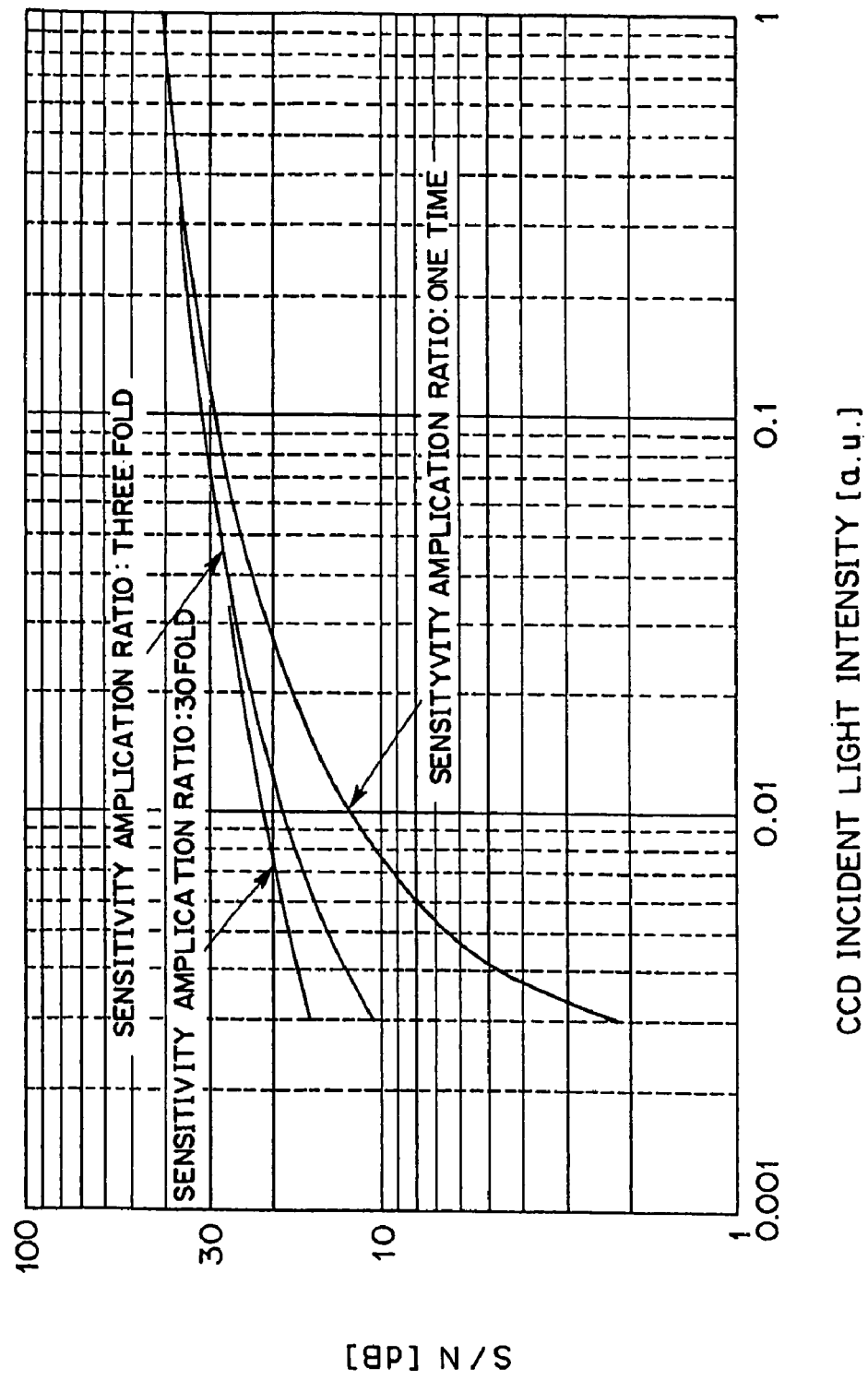
FIG. 10 is a graph showing a CCD sensitivity characteristic (S/N) according to the first embodiment.

FIG. 9 and FIG. 10 show a signal output and S/N characteristic as to the subject intensity which is displayed on the monitor 6 when the sensitivity amplification ratio is changed by changing the voltage value (amplitude) of the sensitivity control pulse φCMD inputted into the charge amplifying section 64.

As shown in the figures, in the gleam region (with small subject intensity), it is characterized in that brightness on the monitor is dark and an image quality (S/N) is low when the sensitivity amplification ratio is one time (no amplification), but a monitor is bright and has high image quality as the sensitivity amplification ratio increases.

The mode switching means 50 is a switch for an operator to select an observation mode between the normal light mode and the special light mode (fluorescent observation).

A place to put the mode switching means 50 in may be at the processor 3, the light source 5, the endoscope 2, or all of them.

The mode switching signal from the mode switching means 50 is outputted to the rotating filter switching means 46, the RGB rotating filter controlling means 47, the photometry means 37, the CCD driving means 31, the CCD sensitivity controlling means 32, and the digital processing circuit 35.

Next, the light source device 5 will be described in detail.

The lamp 40 generates an illumination light from a Xenon lamp, a halogen lamp, an LED, an LD (semiconductor laser) or the like.

The condenser 45 condenses bundle of rays of illumination lights guided from the lamp 40 through the aperture 41, the RGB rotating filter 43, on the back-end surface of the light guide 11.

The aperture 41 and the RGB rotating filter 43 are inserted between the lamp 40 and the condenser 45. The RGB rotating filter 43 is connected to an axis of rotation of the motor 44 in a rotatable manner, and its rotation is controlled at a predetermined speed by the RGB rotating filter controlling means 47.

The RGB rotating filter controlling means 47 is adapted to be able to control the rotation speed of the RGB rotating filter 43 (motor 44) to a predetermined rotation speed by the mode switching signal from the mode switching means 50. The RGB rotating filter controlling means 47 can extend an exposure time by making the rotation speed in the special light mode slower than that of the normal light mode.

The screen average value is inputted from the photometry means 37 to the aperture controlling means 42, where the screen average value and the monitor brightness target value set by an operator is compared. The operator can set brightness of a monitor screen from the brightness setting means provided to the light source device 5 or the signal processing device 4 (not shown).

The aperture controlling means 42 controls from the comparison result (relationship of big and small), the amount of light to the backside of the light guide 11 by controlling opening and closing operation of the aperture 41 which is placed between the lamp 40 and the RGB rotating filter 43.

Figure 11:
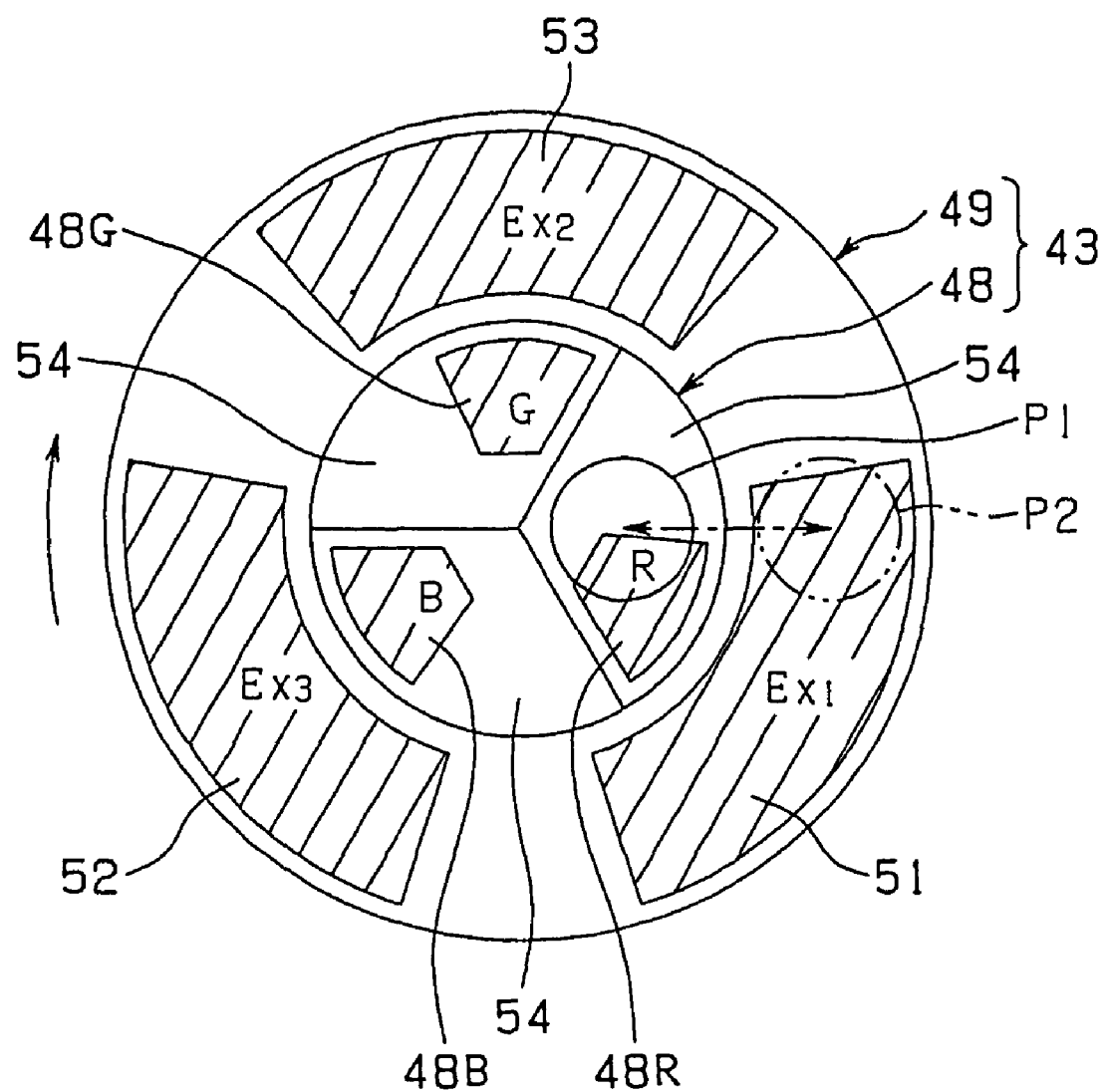
FIG. 11 is a plan view showing a configuration of a RGB rotation filter according to the first embodiment.

The RGB rotating filter 43 has a double configuration with two sets of filter sets 48, 49 in an inner circumference and an outer circumference as shown in FIG. 11.

As shown in FIG. 1, the rotating filter switching means 46 selectively places either the first filter set 48 at the inner circumference side or the second filter set 49 at the outer circumference side of the RGB rotating filter 43 on the illumination light channel shown in FIG. 11 onto an optical axis of an illumination light which connects the lamp 40 and the back-end surface of the light guide 11, by moving the entire of the RGB rotating filter 43.

In the normal light mode, the rotating filter switching means 46 places a filter set 48 at the inner circumference side onto the illumination light channel from the lamp 40 (make an optical beam P1 (solid line in FIG. 11) from the lamp 40 incidence on the filter set 48 at the inner radius side).

In the special light mode, the rotating filter switching means 46 places a filter set 49 at the outer radius side from the lamp 40 onto the illumination light channel (make an optical beam P2 (dashed line in FIG. 11) from the lamp 40 incidence on the filter set 49 at the outer radius side).

As shown in FIG. 11, the first filter set 48 in the inner circumferential part of the RGB rotating filter 43 comprises three filters of R, G, B for the normal light mode, having filters 48R, 48G, 48B with spectral characteristics which transmits the wavelength bands of red (R), green (G), and blue (B).

The second filter set 49 in the outer circumferential part is provided with three filters 51, 52, 53 of Ex1, Ex2, Ex3 with spectral characteristics for the special light mode (fluorescent observation).

For example, in the embodiment, the filter 51 of Ex1 is a filter for an excitation light which transmits the 390-470 nm region.

The filter 52 of Ex2 is a filter for a reflected light, having the center wavelength of near 550 nm, a narrow band of a full width at half maximum at not much more than 10 nm, and spectral characteristics of transmissivity at not much more than a few percent.

The filter 53 of Ex3 is a filter for a reflected light, having the center wavelength of near 600 nm, a narrow band of half-value at not much more than 10 nm, and spectral characteristics of transmissivity at not much more than a few percent.

Figure 12:
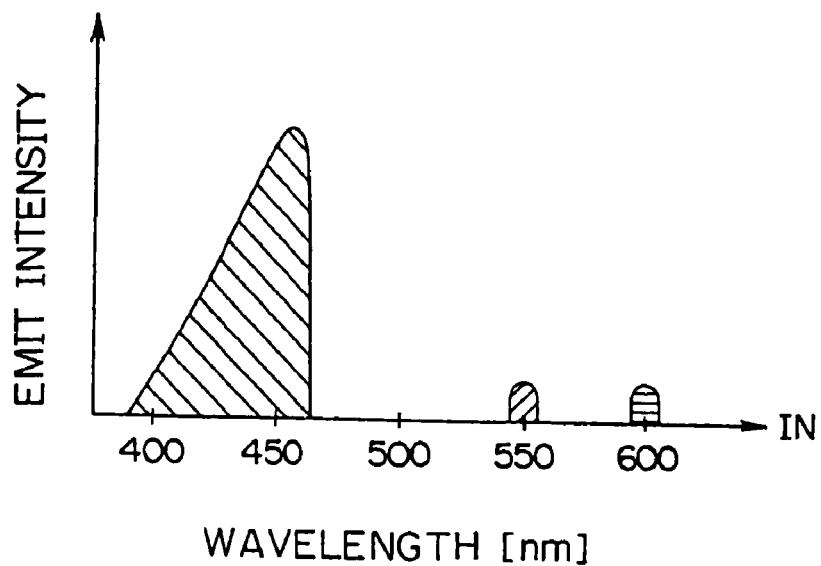
FIG. 12 is a graph showing spectral characteristics of a light source device in fluorescent observation according to the first embodiment.

In the special light mode, an illumination light emitted from the illumination lens 13 of the endoscope 2 has a spectral characteristics as shown in FIG. 12, for example.

The filters 48R, 48G, 48B correspond to exposure time periods of the CCD 19, and light-shielding sections provided among respective filters 48R, 48G, 48B correspond to time-shielding time periods (reading out time periods) of the CCD 19. That is the same in the second filter set 49.

The respective sizes of the second filter set 49 for the special light observation are made bigger than those of the first filter set 48 for the normal light observation. This is because that an exposure time is longer in the special light observation than in the normal light observation.

Although the filters 48R, 48G, 48B for the normal light are provided on the inner circumference and the filters 51, 52, 53 for the special light are provided on the outer circumference in FIG. 11, they may be placed inversely.

In the embodiment, the memory 22 of the storage device 20 is storage means for storing the plural number of accumulation time for the CCD 19 to accumulate charges.

The CCD driving means 31 is driving means for controlling an accumulation time of the image-pickup device based on the plural number of accumulation time accumulated in the storage means.

The plural number of accumulation time refers to an accumulation time in each of the normal light mode and the special mode and an accumulation time for each of three wavelengths in the normal light mode and the special light mode.

An effect of the endoscope device 1 with such a configuration will be described.

First, usage of the endoscope device 1 will be described below.

An operator connects an endoscope 2 corresponding to a part to be observed among a plurality of endoscopes to the processor 3 to start endoscope examination. That causes the CPU 30 of the processor 3 to read out various kinds of data on the endoscope 2 which are stored in the memory 22 via the CPU 21 of the storage device 20 of the endoscope 2.

Then, each charge accumulation time in the CCD 19 of respective three wavelengths in the normal light mode and the special light mode according to an endoscope type which is one of various kinds of data is also read out from the memory 22 to the CPU 30. The charge accumulation time data is outputted to the CCD driving means 31 according to the observation mode.

Next, a function of the normal light mode and the special light mode (fluorescent observation) will be described.

An operator inserts the inserting section 10 of the endoscope 2 into a body cavity of a patient (a bronchial, an esophagus, a stomach, a large intestine, an abdominal cavity, a chest cavity, a bladder, a womb or the like) and observes.

When the normal light observation (normal light mode) is performed, the rotating filter 43 is such that the first filter set 48 is placed on the illumination light channel and the sensitivity amplification ratio of the CCD 19 is set to one time (with no sensitivity amplitude). As the illumination light emitted from the lamp 40 passes through the first filter set 48, field sequential illumination lights of R (red), G (green), B (blue) are emitted from the illumination lens 13 via the light guide 11 of the endoscope 2 to a living body tissue in a chronological order.

The CCD driving means 31 outputs the electronic shutter pulse φOFD in each exposure time of the reflected lights of R, G, B to the CCD 19 based on data of each accumulation time of R, G, B in the normal light mode inputted from the CPU 30, controls a pulse time period which is charge-cleared, and performs desired accumulation time control.

The accumulation time of charges of pixels in the CCD 19 is shorter than that in the general endoscope without mounting a sensitivity variable CCD. As a self-fluorescent is slight, the amount of light to be incidence on the photo-receiving surface of the CCD 19 needs to be big, and the light guide 11 increases the number of light guide fibers more than that in a general endoscope, and the objective lens 14 is designed to mount a lens brighter than that used in a general endoscope.

If the normal light observation is performed, it has bigger incidence intensity to the photo-receiving surface of the CCD 19 than in a general endoscope. Therefore, the accumulation time is set according to the type of the endoscope so as to adjust the amount of incidence by shortening the accumulation time.

The photometry means 37 calculates brightness signals displayed on a monitor screen and outputs them to the aperture controlling means 42. The aperture controlling means 42 compares the brightness signal and the reference value (target value) of a monitor brightness which is set by the operator, and performs opening and closing control of the aperture 41 according to the comparison result (big or small).

When the monitor screen (brightness signal) is brighter than the reference value, the aperture controlling means 42 operates the aperture 41 in the closing direction (illumination intensity to the back-end side of the light guide 11 becomes smaller). On the other hand, if the monitor screen is darker than the reference value, the aperture 41 is operated in the opening direction (illumination intensity to the back-end surface of the light guide 11 becomes bigger). As such, the endoscope device 1 performs automatic light adjustment operation (light adjustment by controlling opening and closing of the aperture of the light source device 5) by controlling the aperture 41 so as to change an illumination intensity to a tissue of a living body and keep the lightness of the monitor 6 at a value set by the operator.

The reflected lights of R, G, B from the tissue of a living body are incidence to the CCD 19 in order. The CCD output signals corresponding to the reflected light of R, G, B from the CCD 19 are inputted into the signal processing device 4, subjected to various kinds of signal processing at the analog processing circuit 33 and the digital processing circuit 35, and outputted to peripheral appliances such as the monitor 6, the storage means and the like. That causes a normal light image to be displayed or stored on the monitor or in the peripheral appliance.

The monitor 6 can obtain the output signals and an S/N characteristic corresponding to the sensitivity amplification ratio of one time as shown in FIG. 9 and FIG. 10.

If fluorescence observation (special light mode) is to be performed, the operator selects the special light mode (fluorescent observation) by a mode switching switch or the like which is provided in the endoscope 2 or the processor 3 that are constituting the mode switching means 50. In response to the selection instruction, the rotating filter switching means 46 places the second filter set 49 of the RGB rotating filter 43 on the illumination light channel. As incident light intensity to the CCD 19 is small, the aperture controlling means 42 keeps the aperture 41 to the almost fully opened place.

When the endoscope 2 approaches to or enlarges the tissue of a living body, the incidence intensity of fluorescent to the CCD 19 increases, and even if the sensitivity amplification ratio of the charge amplifying section 64 is one time (with no amplification), the monitor screen may be saturated. In such a case, the aperture controlling means 42 controls the aperture in the closing direction, which controls for adjusting the amount of light emitted on the subject.

For the illumination light emitted from the lamp 40 of the light source 5, a blue band which is the excitation light of the filter Ex1, a green narrow band light of the filter Ex2, and a red narrow band light of the filter Ex3, which are generated by passing through the second filter set 49 of the RGB rotating filter, are respectively incident on the back-end surface of the light guide 11 via the condenser 45, and emitted as an illumination light with a spectral characteristics (spectrum, intensity) as shown in FIG. 12, for example, onto the tissue of a living body from the illumination lens 13 mounted on the distal portion 12 of the endoscope 2.

Based on the accumulated time data of fluorescent, green reflected light, and a red reflected light in the special light mode (fluorescent observation) inputted from the CPU 30, the CCD driving means 31 controls a charge-clearing pulse width (time period) of the electronic shutter pulse φOFD when capturing an image picked up based on a fluorescent wavelength and two wavelengths of lights reflected to the CCD 19 and controls to make it a desired accumulation time. As to the accumulation time of a fluorescent wavelength and two wavelengths of reflected lights, that of fluorescent is longer than that of the two wavelengths of reflected lights, the pulse width of the electronic shutter pulse φOFD is wider in fluorescent than the two wavelengths of reflected lights.

Figure 13:
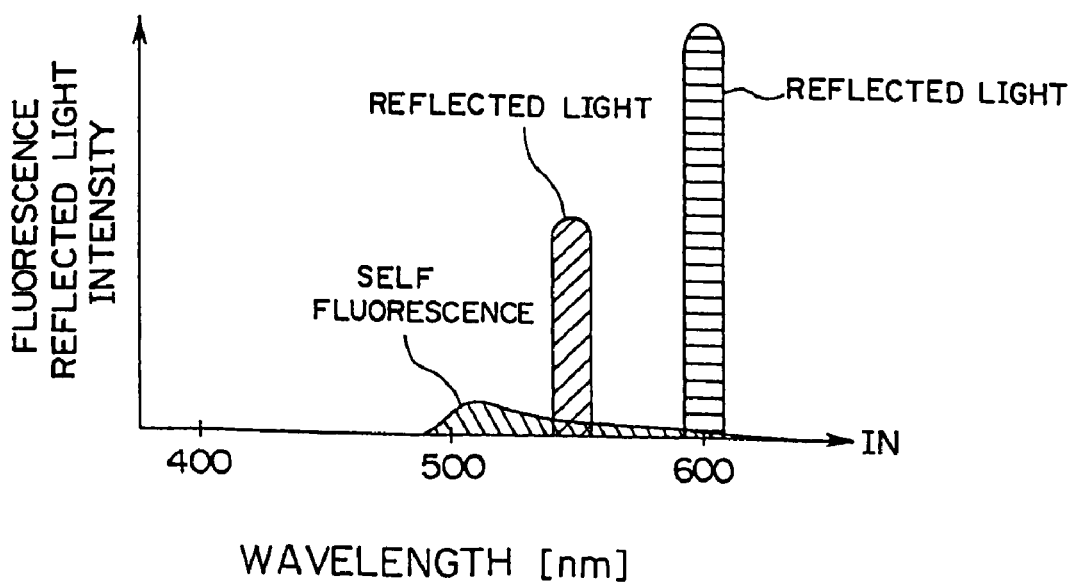
FIG. 13 is a graph showing spectral characteristics of fluorescence and a reflected light in fluorescent observation according to the first embodiment.

The self fluorescent intensity is quite slight compared with the reflected light intensity and the intensity ratio between a fluorescent wavelength and two wavelengths of reflected lights differs for each part. Therefore, if an illumination light as shown in FIG. 12 is emitted on a normal tissue of a living body, spectra of a self fluorescent wavelength and two wavelengths of reflected lights as shown in FIG. 13, for example, are obtained at a part (a kind among a plurality of kinds of endoscopes) on the photo-receiving surface of the CCD 19.

The intensity ratio among respective wavelengths is assumed to be about fluorescence: green reflected light (green narrow band): red reflected light (red narrow band)=1:5:10, for example.

For the accumulation time TA of each wavelength in the special light mode, fluorescence=TE, a green reflected light is 0.2*TE, a red reflected light is 0.1*TE are stored in the memory 22, for example, and if an image based on fluorescence wavelength and two wavelengths of the reflected lights are captured in the accumulation time, they become a screen average value at an equivalent level for each wavelength. As such, an image based on fluorescence is captured in an accumulation time longer than two wavelengths of the reflected light. If the intensity ratio between the fluorescence and the reflected light differs great in the other parts, the CPU 30 calculates an accumulation time of a fluorescence wavelength and two wavelengths of the reflected lights in consideration of the intensity ratio. The memory 22 stores optimal accumulation time data for each type of endoscope.

The photometry means 37 calculates a screen average value of a combined image of fluorescence and reflected lights relating to brightness of the monitor screen, and outputs the result to the CCD sensitivity controlling means 32 and the aperture controlling means 42.

The CCD sensitivity controlling means 32 compares the screen average value and the reference value of monitor brightness (target value) which is set by the operator, and controls a voltage value (amplitude) of the sensitivity control pulse φCMD outputted from the CCD driving means 31 to the CCD 19 to perform control of the sensitivity amplification ratio of the charge amplifying section 64 of the CCD 19 according to the comparison result (big and small).

If the monitor screen is brighter than the reference value, the CCD sensitivity controlling means 32 decreases the sensitivity amplification ratio by further decreasing the voltage value of the sensitivity control pulse φCMD. On the other hand, if the monitor screen is darker than the reference value, the CCD sensitivity controlling means 32 increases the sensitivity amplification ratio by further increasing the voltage value (amplification) of the sensitivity control pulse φCMD.

With the operation, an automatic light adjustment operation (AGC by sensitivity amplification ratio control of the charge amplifying section 64) is performed by changing the sensitivity amplification ratio of the charge amplifying section 64 of the CCD 19 so that brightness of the monitor 6 is kept to the set value (target value) of the operator for a subject whose lightness changes. An automatic light adjustment control is performed to change the sensitivity amplification ratio of the charge amplifying section 64 of the CCD 19 so that brightness of the monitor 6 is kept to the set value (target value) of the operator even if the sensitivity amplification ratio changes due to change in temperature of the CCD.

Reflected light of the excitation light itself and self fluorescence with a peak near 520 nm which is emitted from a tissue of a living body, due to the excitation light emission to the tissue of a living body, are incidence on the objective lens 14, the excitation light is cut by the excitation light cut filter 15 and only the self fluorescence is incidence on the photo-receiving surface of the CCD 19. The reflected light to the illumination light in a green narrow band and a red narrow band are incidence on the objective lens 14, passes through the excitation light cut filter 15 and incidence on the photo-receiving surface of the CCD 19.

Fluorescence, a green reflected light, and a red reflected light from the tissue of a living body are incidence on the CCD 19 in order. The CCD output signal corresponding to each wavelength from the CCD 19 is inputted into the signal processing device 4 and is subjected to predetermined various signal processing at the analog processing circuit 33 and the digital processing circuit 35, then a fluorescence image is displayed or stored on the monitor 6 or peripheral appliances of a personal computer or the like.

In the digital processing circuit 35, a white balance coefficient is switched to a set value of the special light mode (fluorescent observation) different from the normal light mode stored in the memory 22 in capturing images based on fluorescence, a green reflected light and a red reflected light. In the color conversion processing, an output from each wavelength is subjected to color conversion, such that the fluorescence is outputted to a G channel and the red reflected light is outputted to a B channel and the green reflected light is outputted to an R channel, for example.

That makes the monitor 6 to obtain an output signal and S/N characteristic corresponding to any sensitivity amplification ratio as shown in FIG. 9 and FIG. 10. Particularly in a slight light region, when a voltage value (amplitude) of the sensitivity control pulse φCMD to the charge amplifying section 64 of the CCD 19 is changed and the sensitivity amplification ratio increases, the monitor 6 is made to obtain an output signal and S/N character corresponding to the sensitivity amplification ratio threefold, tenfold or the like. The sensitivity amplification ratio is not only amplified to threefold or tenfold but also amplified to any value when a voltage value (amplitude) of the sensitivity control pulse φCMD is controlled.

In the fluorescence observation, for example, when an excitation light in a blue region is emitted on a mucosa, self fluorescence with a peak near 520 nm is obtained. The fluorescence observation uses the characteristic that the intensity ratio of the self fluorescence against the excitation light becomes small in the affected part against the normal part.

By using influence of blood, i.e., a green reflected light which can acutely capture a hemoglobin absorption band, and a red reflected light as a reference light (wavelength band with no influence of blood), a combined image obtained by capturing an image of the observed part is an image in which the presence of a lesion except for influence of inflammation (blood) can be acutely detected. For example, by fluorescence observation, inflammation or hyperplasia is displayed in the same color as that of the normal tissues and a part of an adenoma or cancer is displayed in the color different from that of the normal tissues. That makes an adenoma lesion to be picked up easier than in a usual observation.

In the signal processing device 4 in the embodiment, as described with reference to FIG. 5A to FIG. 5C and FIG. 6A, if a white spot as a defective pixel is present in the previous stage of the CDS IC72 for analog processing or the A/D converter 34 for A/D converting, the digital processing circuit 33 clamps a signal of the dummy section 63 which is unaffected by a white spot as a reference signal, instead of clamping a largely influenced signal in a pixel of the horizontal line of the OB area 61. Therefore, it can perform analog processing without being influenced by a white spot (specifically, it can prevent an image quality from being degraded with a pattern in black lines or the like appearing on the image).

If a signal in the dummy section 63 is made as a reference signal, in the dummy section 63, deviation of the black level due to a change in temperature or an amplification ratio cannot be corrected and a small deviation occurs against a signal level of the original OB area 61 (in the part with no white spot is present); but in the digital clamp circuit 74, as correction by digital clamp processing by using image data of all the pixels of the OB area 61 is performed so as not to be influenced by a white spot, a video signal corresponding to an image with the signal level of the original OB area 61 being a black level can be generated without being virtually influenced by a white spot.

Accordingly, the embodiment has an effect as below.

As such, according to the embodiment, a signal which is unaffected by a defective pixel in the dummy section 63 is analog-clamped as a reference signal, while the signal in the OB area 61 in which a defective pixel may be present is not analog-clamped and a slight deviation occurs between a signal level of the dummy section 63 and an inherent signal level of the original OB area 61 in a part where no defect image is present, but image quality degradation due to a defective pixel such as a white spot in the OB area 61 can be virtually avoided by digital-clamping by using all the number of pixels in the OB area 61 which is sufficiently larger than the number of pixels in the horizontal direction in the OB area 61.

Without using all the number of pixels in the OB area 61, image quality degradation due to a defective pixel such as a white spot in the OB area 61 may be alleviated by digital-clamping by using the number of pixels more than the number of pixels in the horizontal direction in the OB area 61.

According to the embodiment, various types of data relating to the endoscope 2 stored in the memory 22 of the storage device 20 enable observation based on optimum information, as required, according to the type of the endoscope (a part to be observed).

When stored data is read in and controlled, control becomes easy. If accumulation time is controlled to be different for each wavelength when fluorescence or a reflected light with greatly different intensities are captured in the special light mode (fluorescence observation), each image based on fluorescence and a reflected light can be captured in an optimal brightness. Therefore, better image quality can be obtained by making fluorescent observation images of the combined images have appropriate brightness.

As a modified example in the embodiment, for example, in the digital clamp circuit 74 in FIG. 5C, addition by the adder 84 and subtraction by the subtracter 85 may be performed except for a pixel in which a white spot is present.

Specifically, as also described in the embodiment 2, address information on a pixel in which a white spot is present as a defective pixel of the OB area 61 in the CCD 19 included in the endoscope 2 is previously written in the memory 22 of each endoscope 2, and the CPU 30 reads the address information on the pixel in which a white spot is present in the OB area 61 stored in the memory 22 of the endoscope 2, which is connected to the signal processing device 4 (of the processor 3), via the CPU 21.

In the modified example, the CPU 30 controls the adder 84 to apply the OB clamp pulse which is missing in a pixel in which a white spot is present, and also makes the number of images, which is the result of the number of pixels in which a white spot is present is subtracted from all the number of pixels of the OB area 61, inputted to the subtracter 85.

With such a configuration, even if a white spot is present in the OB area 61, the influence can be eliminated, enabling the black level to be reproduced accurately. That is to say, a video signal which can also reproduce an image part near the black level can be generated accurately.

Second Embodiment

Figure 14D:
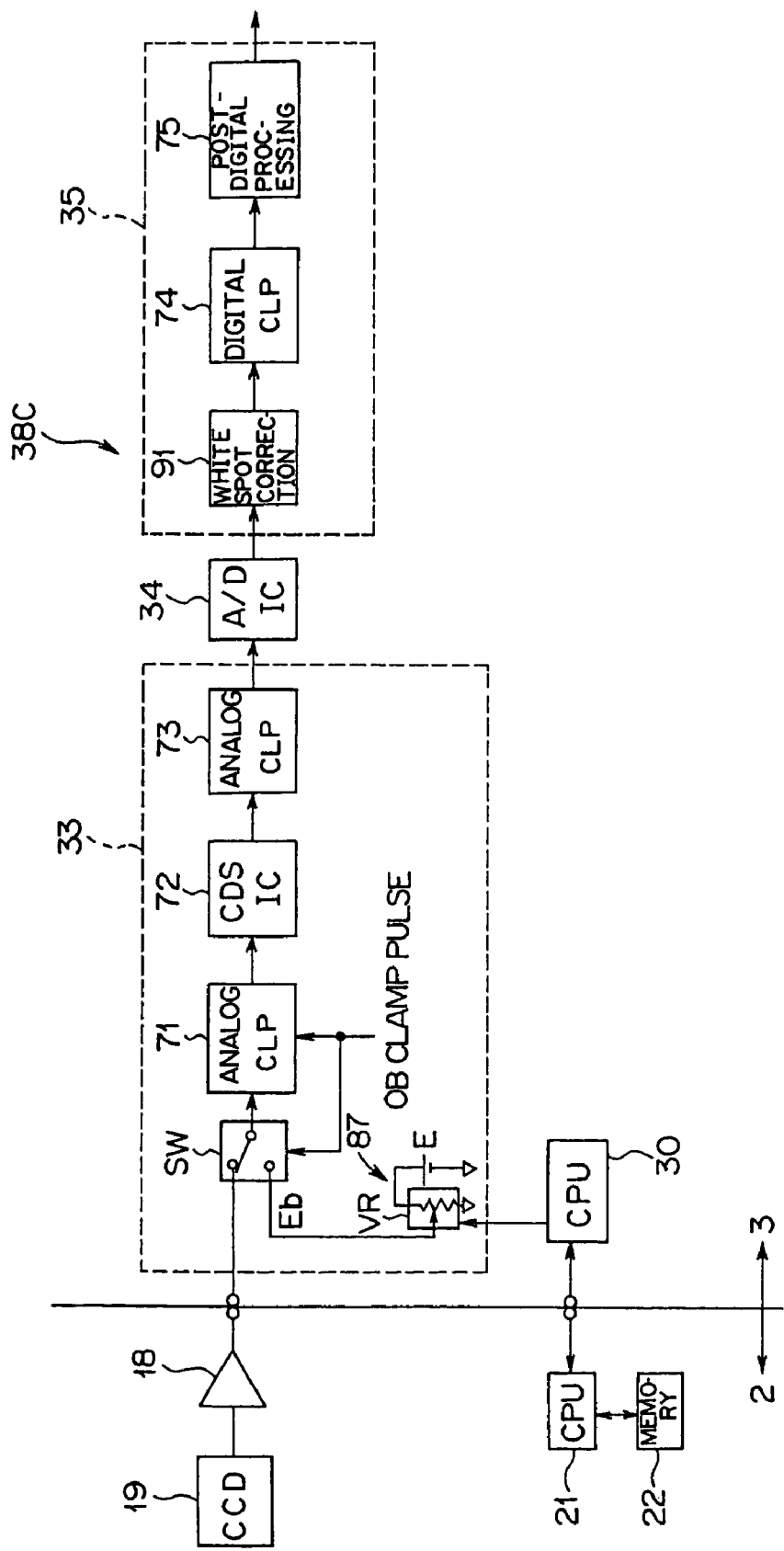
FIG. 14D is a block diagram showing a configuration of a video signal processing circuit in a modified example.

Next, a second embodiment of the present invention will be described with reference to FIG. 14A to FIG. 14D. FIG. 14A shows a configuration of the video signal processing circuit 38B in the second embodiment of the present invention.

The video signal processing circuit 38B has a configuration of the video signal processing circuit 38 of the FIG. 5A provided with a white spot correction circuit (defect pixel correction section) 91 for correcting an influence of a white spot as a defect image before the digital clamp circuit 74.

The white spot correction circuit 91 is, as shown in FIG. 14B, for performing digital image correction on a pixel with a white spot (white spot pixel) 92 as a target pixel by using image data of a surrounding pixel section 93; and as shown in FIG. 14C, for reading out the pixel surrounding region of the white spot 92 on the image data stored in an image memory 94 and performing space filter processing such as averaging on image data of the white spot 92 with values of surrounding pixels by a space filter processing section 95.

In such a case, it is performed on image data of the white spot 92 which is a defective pixel in the OB area 61 and the image area 60 stored in the image memory 94. For that reason, it is adapted to store information on a pixel place (address) of the white spot 92 of the OB area 61 and the image area 60 in the CCD 19 included in the each endoscope 2, for example, in the memory 22.

The CPU 30 in the signal processing device 4 reads out the information from the memory 22 of the connected endoscope 2 via the CPU 21, and sends it to the space filter processing section 95, where white correction processing is performed on the image data of the white spot 92 based on the information. Specifically, the image data of the white spot 92 is replaced with an image data value which is subjected to space filter processing such as an average value or weighted mean on the surrounding pixel section 93, and an influence of the white spot 92 will be almost eliminated. The other configuration is the same as the first embodiment.

According to the embodiment, the analog clamp processing in the analog processing circuit 33 is the same operation as that of the first embodiment. On the other hand, in the digital clamp processing in the digital processing circuit 35, image data of the white spot 92 in the OB area 61 is replaced with an average value or the like calculated by the surrounding pixel section 93 and adapted not to use image data of the white spot 92, and it can reproduce the black level more accurately than the first embodiment (alternatively, the same effect can be obtained as the modified example of the first embodiment). Correction of the white spot 92 in the OB area 61 may be simply replaced with an average value of pixel data at both sides (normal one, which is not the white spot 92) such as in the horizontal direction of the pixels of the white spot 92.

According to the embodiment, as pixels of the white spot 92 in the image area 60 is appropriately replaced or the like with image data of surrounding pixel section 93, an image with a good image quality in which almost all of the white spots 92 are eliminated can be obtained.

In FIG. 14C, although image data is once stored in the image memory 94 and correction is performed on image data of the white spots 92 in the space filter processing section 95, it may be adapted to perform space filter processing at the previous stage of the image memory 94.

In the first and the second embodiments, although analog clamp processing is performed at the timing when signals from the dummy section 63 are inputted in the analog clamp circuit 71 or 73, it is not limited to that and may have a configuration of FIG. 14D, for example.

FIG. 14D shows a configuration of a video signal processing circuit 38C and the surrounding sections of a modified example of the second embodiment.

As to the video signal processing circuit 38C, for example, in the video signal processing circuit 38B of FIG. 14B, further in the analog processing circuit 33, a reference voltage generating circuit 87 for generating a reference voltage Eb of the black level and the switching switch SW for switching signals inputted into the analog clamp circuit 71 are provided.

Although the switching switch SW is generally in a state of inputting a signal at the side of CCD 19 into the analog clamp circuit 71, at the timing (OB time period) for signals in the OB area 61 to be inputted into the analog clamp circuit 71, for example, the reference signal Eb is switched to be inputted into the analog clamp circuit 71 by the OB clamp pulse. Then, the analog clamp circuit 71 clamps the reference voltage Eb.

The reference voltage generating circuit (direct current generating circuit) 87 makes a predetermined direct current voltage E partial pressure with a resistance value by an electronic volume VR and generates a current reference voltage Eb, for example. The resistance value of the electronic volume VR can be electrically controlled by the CPU 30.

The value of the reference voltage Eb (signal level) is preferably set so that it becomes the original signal level in a part where white spots are not present in the OB area 61 of the CCD 19 according to the actually connected CCD 19. As an output signal from the CCD 19 is adapted to be inputted into the analog clamp circuit 71 via the preamp 18 in FIG. 14D, the value of the reference voltage Eb is set to match with the value which is actually the original signal level in the OB area 61 amplified by the preamp 18.

Correspondingly, in the modification, the information, i.e., the information on a value which is the original signal level in the OB area 61 of the included CCD 19 amplified at the preamp 18 is previously stored in the memory 22 in the endoscope 2 containing the CCD 19.

When the detachable endoscope 2 is freely detachably connected to the processor 3, the CPU 30 controls so that information unique to the CCD 19 of the endoscope 2 is read out from the memory 22 via the CPU 21, the resistance value of the electronic volume VR is controlled by the read out information, and the reference voltage Eb of the signal level near the signal level of the OB area 61 of the CCD 19 is generated.

With such a configuration, direct current reproduction of the black level near the signal level of the OB area 61 of the CCD 19 actually included in the endoscope 2 can be performed. That is to say, in the case where the signal level of the OB area 61 differs according to the type of the CCD 19, and also in the case of the CCD 19 with individual differences in the same kind, direct current can be reproduced for the black level near characteristic of the CCD 19.

Although the reference voltage generating circuit 87 is provided in the analog processing circuit 33 in the modification, it may be provided inside the endoscope 2 such as in an operation section, a connector section or the like. In FIG. 14D, the output signal from the CCD 19 is shown in the case where it is inputted into the analog processing circuit 33 via the preamp 18, it may be adapted to be inputted into the analog processing circuit 33 without passing through the preamp 18.

In the modification, it is described by an example where analog clamp is performed in a signal time period of the OB area 61. Therefore, in this case, a clamp pulse does not need to be used in the signal time period of the dummy section 63. It is a matter of course that it can be analog clamped in the dummy time period as in the embodiment 1 or the embodiment 2.

The level of the abovementioned reference voltage Eb may be set slightly lower than the original signal level in the OB area 61 (signal level of the OB area 61 indicates temperature dependency) in a usual usage (for example, a state of temperature when it is used as inserted in a body). Alternatively, it may be set to the original signal level or lower in the OB area 61.

For example, as a difference signal corresponding to a difference between a signal level of the dummy section 63 and a signal level of the original OB area 61 is outputted from the subtracter 85 in FIG. 5C, the difference signal may be used as information for estimating temperature of the CCD 19.

That is to say, as a signal in the dummy section 63 does not influence temperature but the signal level of the OB area 61 increases as temperature does, the signal can be used for estimating temperature of the CCD 19 by the value of the difference signal.

As the white spot is largely influenced by temperature, an accumulation time and the set sensitivity amplification ratio or the sensitivity control pulse φCMD, it can be used for estimating temperature or the sensitivity amplification ratio of the CCD 19 by the output signal from a pixel of the white spot.

For example, it is principally possible to add up a plurality of signals from the white spots or the like based on information on pixel places of pixels of white spots stored in the memory 22, and temperature of the CCD 19 or the amplification ratio to be actually set are estimated by a plurality of pieces of information in the case where the sensitivity control pulse ΦCMD is changed and applied.

More specifically, known temperature and a predetermined sensitivity control pulse ΦCMD are previously changed, output signal level from the CCD 19 is measured in each case, and stored in the memory 22. When it is actually used, the sensitivity control pulse ΦCMD is changed and the output signal level from the CCD 19 is measured, and temperature or amplification ratio of the CCD 19 is estimated from the information nearest to the information stored in the memory 22.

Then, for example, values of the estimated temperature or the amplification ratio of the CCD 19 is displayed on a screen of the monitor 6, or used for controlling the amplification ratio. Alternatively, in the OB area 61, that the white spots are intentionally formed in great number is prepared, and information on the white spots in the part may be used for estimating temperature or amplification ratio. Particularly, if temperature estimation or amplification ratio estimation is performed from the signal level of the white spots in particularly the parts other than the image area 60, such as in the OB area 61, it does not overlap the signal time period of the image area 60, and the processing of the estimation will be easily performed.

Embodiments configured by combining part of the above-mentioned embodiments are included in the present invention.

What is claimed is:

1. A signal processing device for an endoscope characterized by comprising:
    an analog signal processing circuit that processes an analog output signal outputted from a solid image-pickup device, which has an image area and an optical black area performing photoelectric conversion, includes a function of varying an amplification ratio, and is mounted on the endoscope, to extract signal components photoelectrically converted by the image area;
    a first signal clamp circuit for clamping an analog reference signal which is unaffected by a defective pixel in the optical black area so as to adjust into an input range of the analog signal processing circuit and inputting it to the analog signal processing circuit; and
    a second signal clamp circuit for, with respect to the output signal from the analog signal processing circuit, clamping the signal in the optical black area using output signals of at least the number of pixels larger than the number of pixels in a horizontal direction in the optical black area.

2. The signal processing device for an endoscope according to claim 1, characterized in that the first signal clamp circuit clamps the analog reference signal outputted from the inside of the solid image-pickup device.

3. The signal processing device for an endoscope according to claim 1, characterized in that the first signal clamp circuit clamps the analog reference signal generated in the signal processing device for an endoscope.

4. The signal processing device for an endoscope according to claim 2, characterized in that the first signal clamp circuit clamps a signal in a dummy section without a function of photoelectric conversion that is provided for transferring pixels in the image area and the optical black area as the analog reference signal.

5. The signal processing device for an endoscope according to claim 1, characterized in that the first signal clamp circuit clamps a direct current voltage generated from a direct current voltage generating circuit as the analog reference signal in a time period during which pixels of the optical black area are inputted.

6. The signal processing device for an endoscope according to claim 1, characterized in that the second signal clamp circuit is a digital signal clamp circuit for clamping a signal of the optical black area by using output signals of at least the number of pixels larger than the number of pixels in a horizontal direction in the optical black area to a digital signal converted from an output signal of the analog signal processing circuit.

7. The signal processing device for an endoscope according to claim 1, characterized in that a value of the direct current voltage can be set for each of the solid image-pickup device mounted on the endoscope.

8. The signal processing device for an endoscope according to claim 1, characterized by comprising a defective pixel correction circuit for outputting a defective pixel correction signal to the second signal clamp circuit, the defective pixel correction signal being corrected for the defective pixel for at least the output signal of pixels of the optical black area in the output signal of the analog signal processing circuit.

9. The signal processing device for an endoscope according to claim 8, characterized in that the defective pixel correction circuit generates the defective pixel correction signal by correcting image data of the defective pixel with a processing value using image data of surrounding pixels.

10. The signal processing device for an endoscope according to claim 8, characterized in that the defective pixel correction circuit generates the defective pixel correction signal by correcting for a defective pixel in an image area with image data of surrounding pixels.

11. The signal processing device for an endoscope according to claim 1, characterized in that the reference signal is set to an output signal level or lower when no defective pixel is present in the optical black area.

12. The signal processing device for an endoscope according to claim 5, characterized in that the reference signal is set to an output signal level or lower when no defective pixel is present in the optical black area.

13. A signal processing device for an endoscope characterized by comprising:
    an analog signal processing circuit that performs signal processing on an analog output signal outputted from a solid image-pickup device, which has an image area and an optical black area performing photoelectric conversion, includes a function of varying an amplification ratio, and is mounted on the endoscope, to extract signal components photoelectrically converted by the image area;
    an analog signal clamp circuit for, with respect to an analog output signal outputted from the solid image-pickup device, clamping a reference signal which is unaffected by a defective pixel in the optical black area so as to adjust into an input range of the analog signal processing circuit;

a defective pixel correction circuit for correcting a defective pixel for at least an output signal of pixels of the optical black area in a digital output signal converted from the output signal of the analog signal processing circuit; and a digital signal clamp circuit for clamping the signal of the optical black area in the output signal of the defective pixel correcting circuit.

14. The signal processing device for an endoscope according to claim 13, characterized in that the analog signal clamp circuit clamps the reference signal outputted from the inside of the solid image-pickup device.

15. The signal processing device for an endoscope according to claim 13, characterized in that the analog signal clamp circuit clamps the reference signal generated in the signal processing device for an endoscope.

16. The signal processing device for an endoscope according to claim 14, characterized in that the analog signal clamp circuit clamps a signal in a dummy section without a function of photoelectric conversion that is provided for transferring a pixel in the image area and the optical black area as the reference signal.

17. The signal processing device for an endoscope according to claim 13, characterized in that the analog signal clamp circuit clamps a direct current voltage generated from a direct current voltage generating circuit as the reference signal in a time period during which pixels of the optical black area are inputted.

18. The signal processing device for an endoscope according to claim 13, characterized in that the digital signal clamp circuit clamps a signal in the optical black area by using output signals of the number of pixels in the horizontal direction and the vertical direction of the optical black area in the output signal in the defective pixel correction circuit.

19. The signal processing device for an endoscope according to claim 13, characterized in that the defective pixel correction circuit corrects image data of the defective pixel with a processing value by using image data of surrounding pixels.

20. A signal processing device for an endoscope characterized by comprising:

an analog signal processing circuit that performs a processing on an analog output signal outputted from a solid image-pickup device, which has an image area and an optical black area performing photoelectric conversion, includes a function of varying an amplification ratio, and is mounted on the endoscope, to extract signal components photoelectrically converted by the image area; and at least a signal clamp circuit of either of a first signal clamp circuit for clamping an analog reference signal which is unaffected by a defective pixel in the optical black area so as to adjust into an input range of the analog signal processing circuit and inputting it to the analog signal processing circuit; or a second signal clamp circuit for, with respect to the output signal from the analog signal processing circuit, clamping the signal in the optical black area using output signals of at least the number of pixels larger than the number of pixels in a horizontal direction in the optical black area.

* * * * *